(12) United States Patent
Littman et al.

(10) Patent No.: US 6,279,882 B1
(45) Date of Patent: Aug. 28, 2001

(54) OXYGENATING APPARATUS, METHOD FOR OXYGENATING A LIQUID THEREWITH, AND APPLICATIONS THEREOF

(75) Inventors: Howard Littman, Schenectady; Kent L. Peterson, Albany, both of NY (US)

(73) Assignee: Life International Products, Inc., Naples, FL (US)

( * ) Notice: Subject to any disclaimer, the term of this patent is extended or adjusted under 35 U.S.C. 154(b) by 0 days.

(21) Appl. No.: 09/559,605

(22) Filed: Apr. 27, 2000

Related U.S. Application Data

(62) Division of application No. 09/067,689, filed on Apr. 28, 1998, now Pat. No. 6,120,008.

(51) Int. Cl.[7] .................................................... B01D 47/02
(52) U.S. Cl. ............................ 261/76; 210/620; 210/758; 210/137; 210/192; 210/205; 210/253; 261/DIG. 75; 261/DIG. 78; 261/DIG. 56; 422/45
(58) Field of Search .................................... 210/620, 758, 210/137, 192, 205, 253; 261/76, DIG. 75, DIG. 78, DIG. 56; 422/45

(56) References Cited

U.S. PATENT DOCUMENTS

| 1,594,947 | 8/1926 | Hartman et al. ........................ 261/76 |
| 2,852,239 | 9/1958 | Vicard .................................... 261/76 |

(List continued on next page.)

FOREIGN PATENT DOCUMENTS

| 2447337 | 4/1976 | (DE) . |
| 0244954 | 11/1987 | (EP) . |
| 0322925 | 7/1989 | (EP) . |
| 0555498 | 8/1993 | (EP) . |
| 2238525 | 7/1974 | (FR) . |
| 2 077 712 | 12/1981 | (GB) . |
| 08155430 | 6/1996 | (JP) . |
| WO 97/27146 | 7/1997 | (WO) . |

OTHER PUBLICATIONS

Jan H. Witte, "Mixing Shocks in Two–Phase Flow", J. Fluid Meech. (1969), vol. 36, part 4, pp. 639–655.

(List continued on next page.)

*Primary Examiner*—Krisanne Thornton
(74) *Attorney, Agent, or Firm*—Baker & Daniels

(57) ABSTRACT

An apparatus and process for oxygenating a liquid. The apparatus includes a liquid pump fluidly connected to an injector having a liquid inlet forming a nozzle, a liquid outlet and an oxygen inlet therebetween, the injector arranged such that the injector liquid inlet is above the injector liquid outlet, and a downwardly opening first diffuser portion connected to the injector outlet. The first diffuser portion is serially connected to a second diffuser portion located below the first diffuser portion. Liquid being pumped by the pump is conducted downwardly through the injector and the first diffuser portion to the second diffuser portion. The process includes the steps of first, introducing a liquid under pressure into the injector and flowing it liquid downwardly through the injector at a selected liquid volume flow rate; second, introducing oxygen into the injector to create an admixture of liquid and large oxygen bubbles; third, introducing the mixture of liquid and large oxygen bubbles from the injector into the first diffuser portion at such velocity to create a shockwave in the first diffuser portion; fourth, breaking up the large oxygen bubbles into a greater number of small oxygen bubbles; fifth, introducing a mixture of liquid and small oxygen bubbles from the first diffuser portion into the second diffuser portion, which may be a continuation of the first diffuser portion and wherein the pressure of the admixture is increased; sixth, floating some of the bubbles upwards against the downward liquid flow and breaking them down to smaller size; continuing the fourth through sixth steps until the smaller bubbles no longer float upwards; and recovering the oxygen-enriched liquid.

24 Claims, 9 Drawing Sheets

U.S. PATENT DOCUMENTS

| | | |
|---|---|---|
| 3,399,511 | 9/1968 | Geiringer .................................. 261/76 |
| 3,761,065 | 9/1973 | Rich et al. .............................. 261/76 |
| 3,774,846 | 11/1973 | Schurig et al. ......................... 261/76 |
| 4,157,304 | 6/1979 | Molvar .................................... 261/76 |
| 4,210,534 | 7/1980 | Molvar .................................... 261/76 |
| 4,224,158 | 9/1980 | Molvar .................................... 261/76 |
| 4,226,719 | 10/1980 | Woltman .............................. 210/220 |
| 4,370,304 | 1/1983 | Hendricks et al. ..................... 261/76 |
| 4,639,340 | 1/1987 | Garrett ............................... 261/36.1 |
| 4,695,378 | 9/1987 | Ackman et al. .................. 210/198.1 |
| 4,867,918 | 9/1989 | Kiyonga et al. ........................ 261/76 |
| 4,885,084 | 12/1989 | Doyle ..................................... 261/76 |
| 5,061,406 * | 10/1991 | Cheng ..................................... 261/76 |
| 5,167,798 * | 12/1992 | Yoon et al. ............................ 209/170 |
| 5,302,286 | 4/1994 | Semprini et al. ..................... 210/610 |
| 5,525,242 * | 6/1996 | Kerecz .................................. 210/758 |
| 5,896,435 | 4/1999 | Gautier et al. ......................... 261/76 |
| 5,904,851 * | 5/1999 | Taylor et al. ......................... 210/620 |
| 5,951,922 | 9/1999 | Mazzei .................................... 261/76 |
| 6,120,008 * | 9/2000 | Littman et al. ......................... 261/76 |

OTHER PUBLICATIONS

C.L. Breins, et al. "Hydrodynamics and Gas Liquid Mass Transfer in Downward Venturi–Bubble Column Combination", Chemical Engineering Science, vol. 47, No. 13/14, pp. 3549–3556 (1992).

P.H.M.R. Cremers et al., "Hydrodynamics and Mass Transfer Characteristics of a Loop–Venturi Reactor with a Downflow Liquid Jet Ejector", Chemical Engineering Science, vol. 47, No. 13/14, pp. 3557–3564 (1992).

R.E. Speece, et al., "Commercial Oxygen Use in Water–Quality Management", Water Environment & Technology, Jul., 1990, pp. 54–61.

Mazzei Injector Corporation Product Catalog, pp. 3, 17, 19, 22, 23, 24, 25.

* cited by examiner

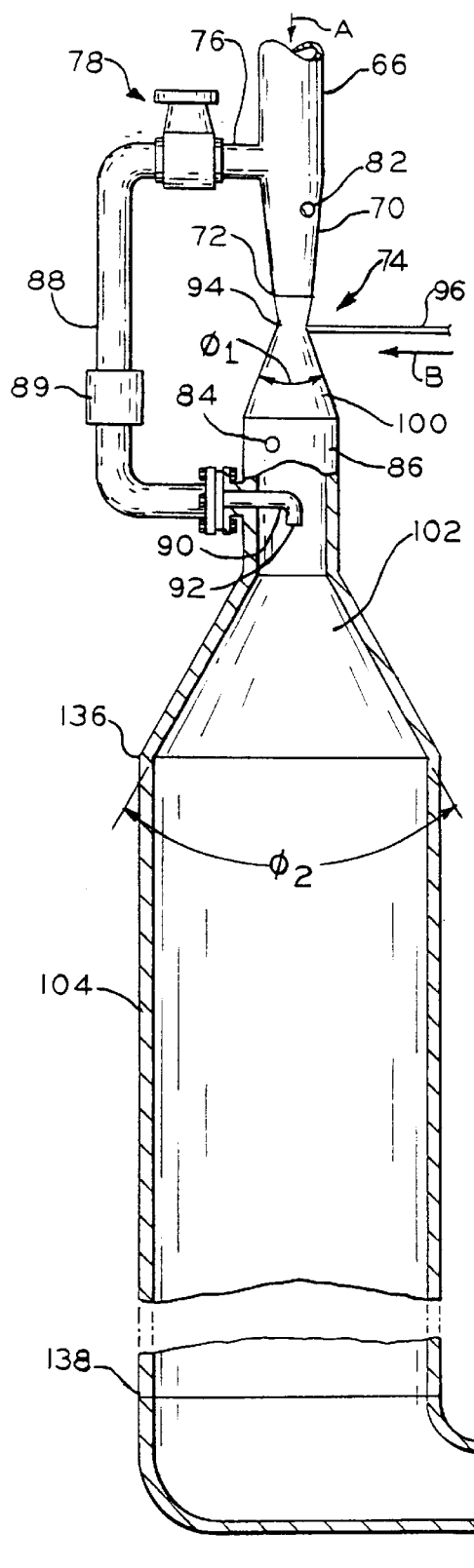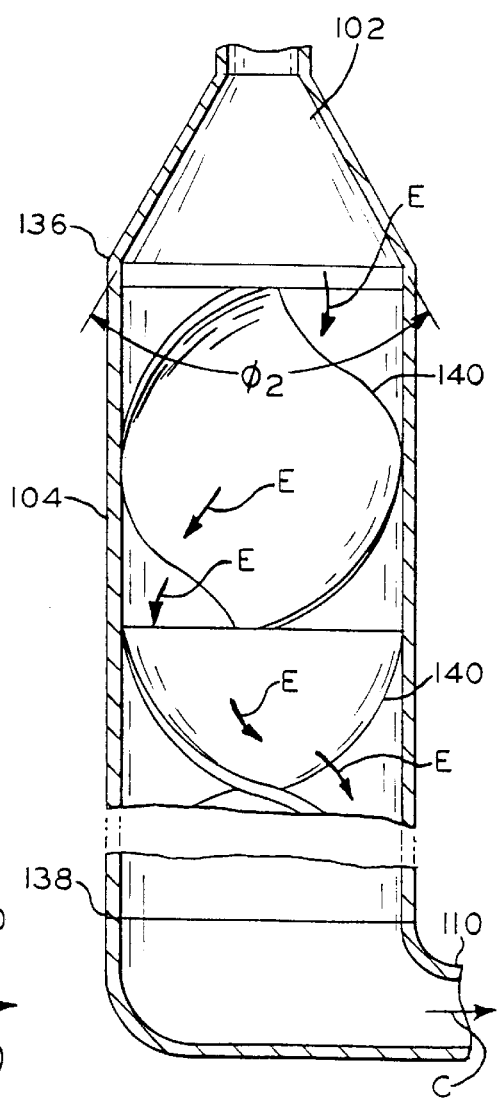
FIG_2A  FIG_2B

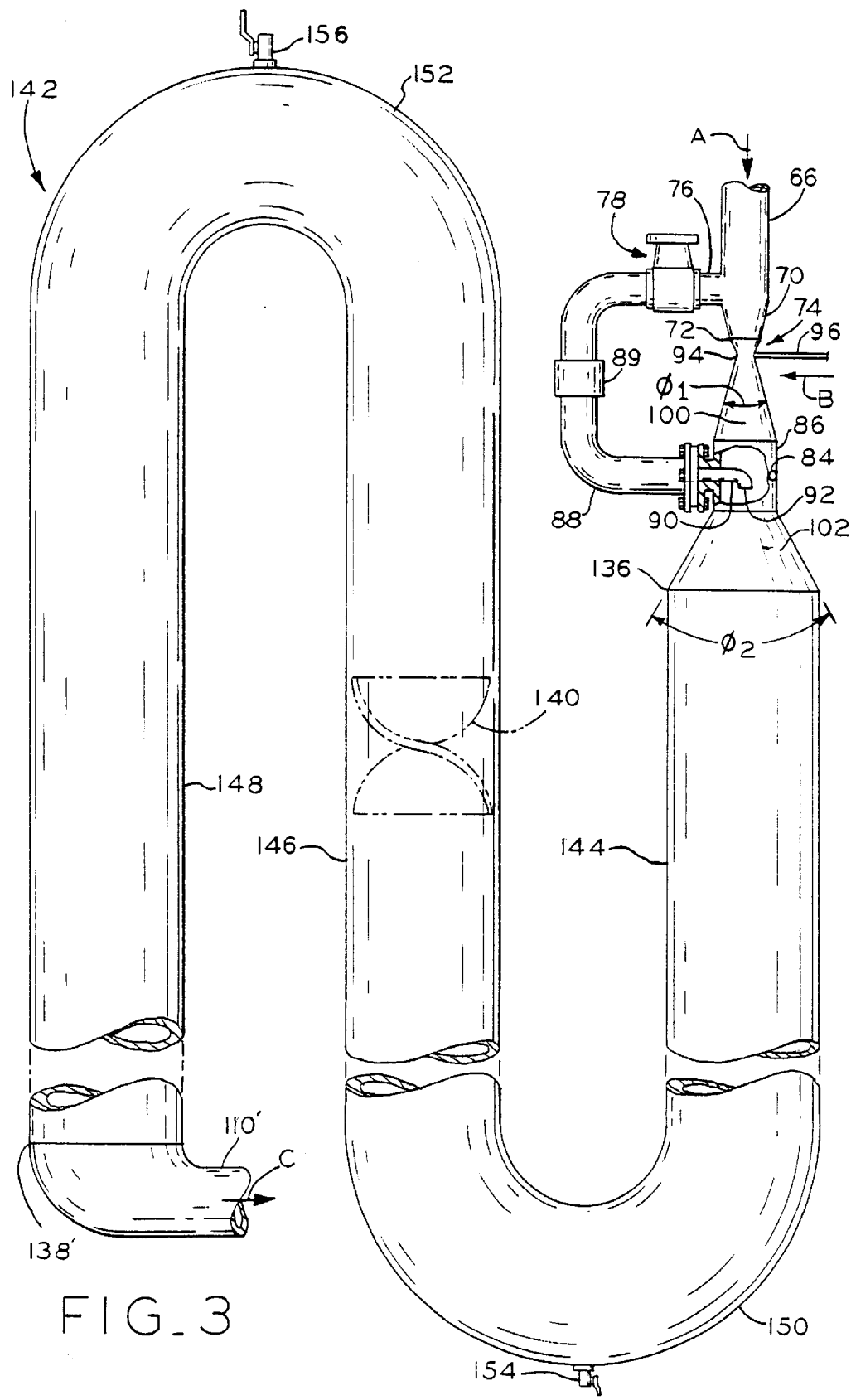
FIG_3

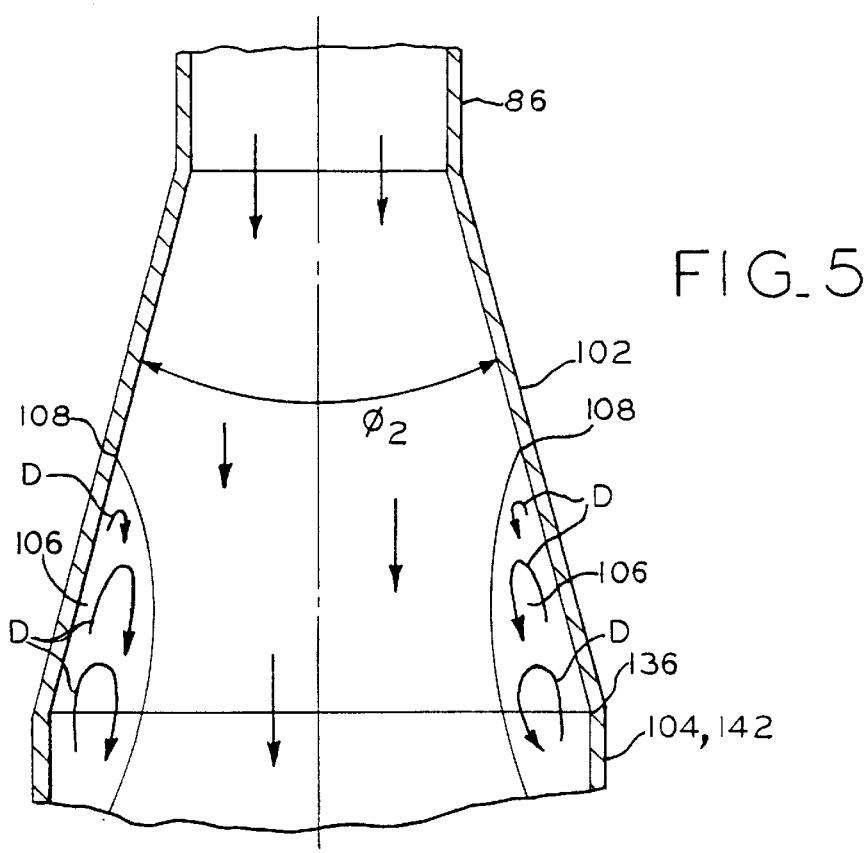
FIG._5
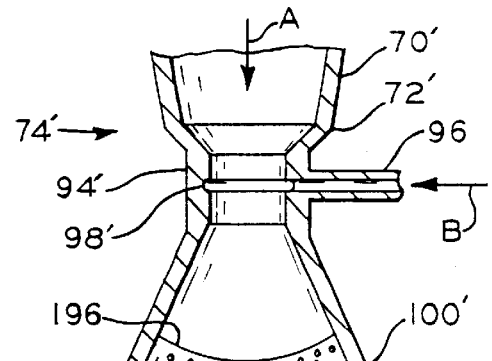
FIG._7

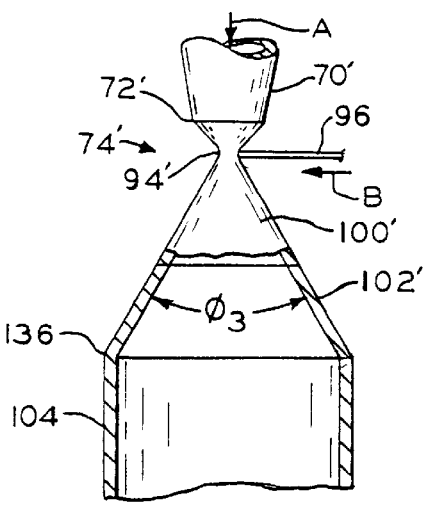
FIG_6A
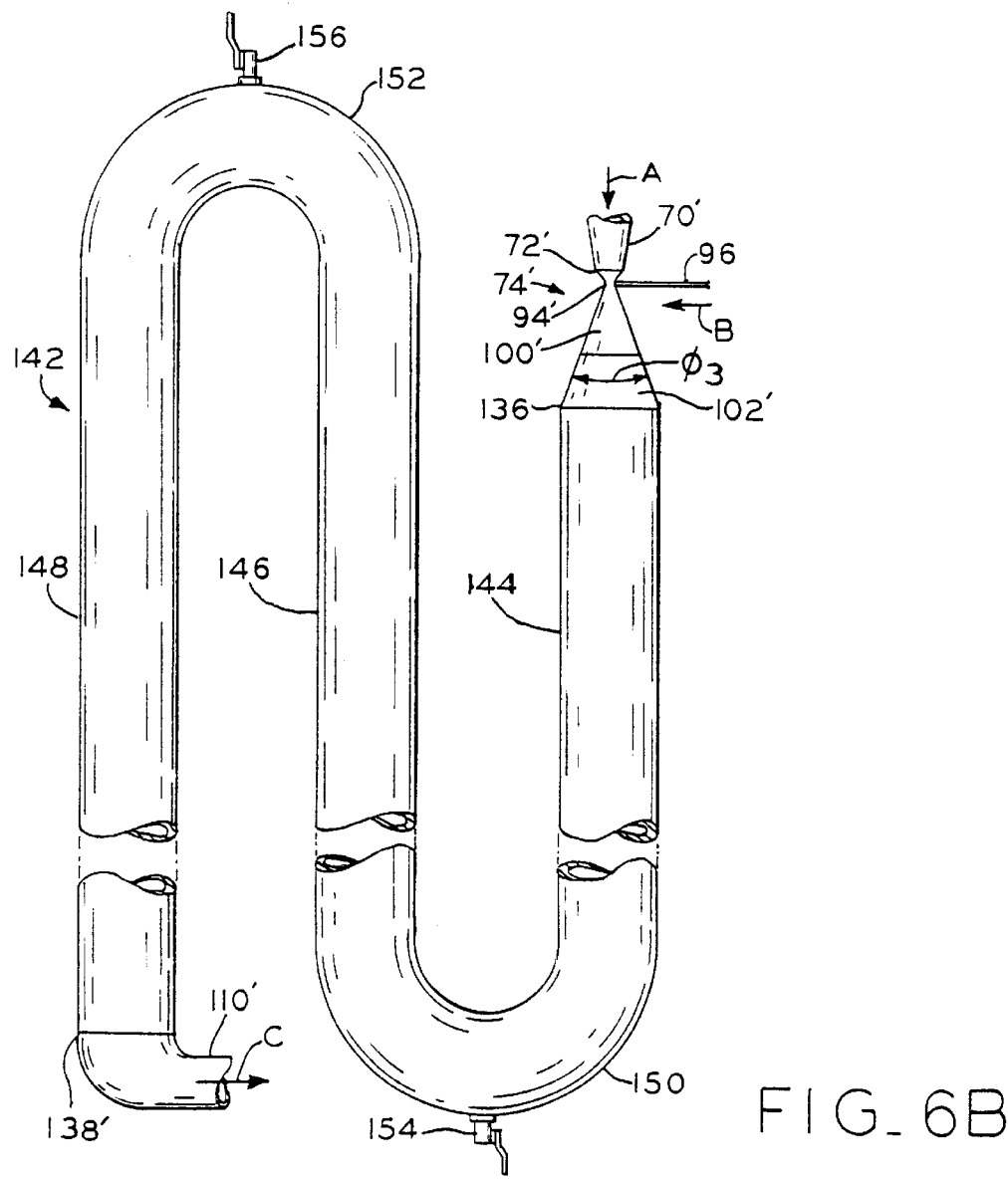
FIG_6B

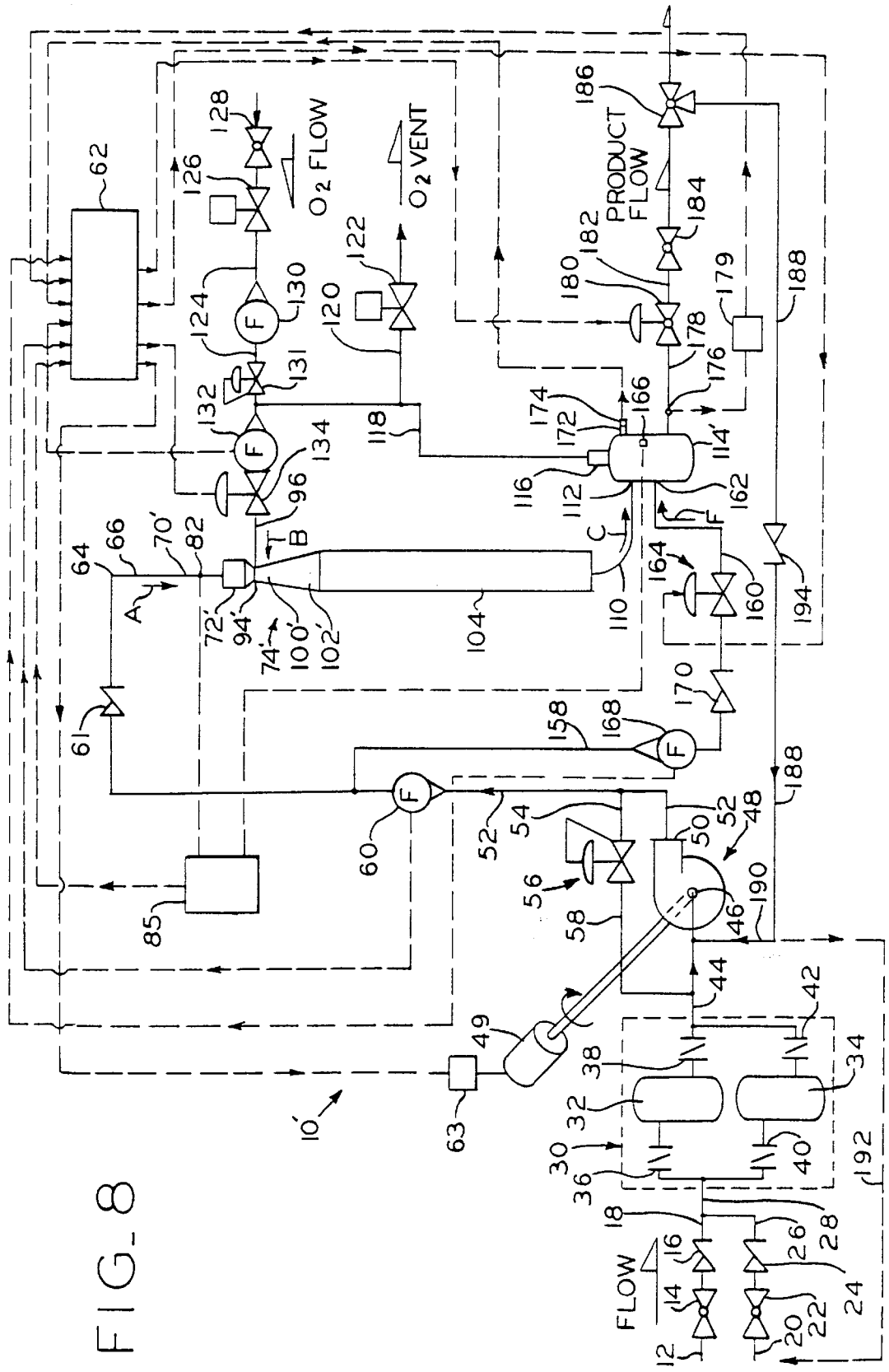
FIG_8

TOTAL OXYGEN FLOW CONTROL LOOP

DISCHARGE PRESSURE CONTROL LOOP

OXYGENATING APPARATUS, METHOD FOR OXYGENATING A LIQUID THEREWITH, AND APPLICATIONS THEREOF

This is a division of application Ser. No. 09/067,689, filed Apr. 28, 1998 U.S. Pat. No. 6,120,008.

BACKGROUND OF THE INVENTION

This invention relates to an apparatus for oxygenating a liquid, such as water, a method for oxygenating the liquid, and applications of liquids oxygenated by the inventive apparatus and method.

It is known that various types of liquids are oxygenated, i.e., prepared in solution with oxygen, to achieve various results. For example, consumption of an oxygen enriched beverage has a favorable effect on well being and physical performance. For example, eight test subjects of various ages and differing sex had their blood oxygen contents and their pulse rates determined. Each subject then drank between ½ and ¾ liters of highly oxygenated water. A short period after ingestion of the enriched water, evidence of a pulmonary function bypass was observed through an average blood oxygen level increase of about 30%, and the effect of a concomitant cardiac relief was observed through an average pulse rate reduction of about 10%. Further, the added oxygen tends to reduce the tartness of any carbonation and does not impart any taste to the resulting liquid.

As a further example, a liquid may be oxygenated to promote bioremediation of contaminated or oxygen-depleted bodies of water, and effective bioremediation requires a high rate of oxygen use. The replenishment of oxygen in groundwater, for example, occurs very slowly. As a result, oxygen levels in the contaminated groundwater systems are often quickly depleted, even when water has been thoroughly aerated before the onset of the bioremediation process. Thus, bioremediation processes are more effective if higher oxygen levels are provided in the groundwater, enabling a desirably greater and more rapid treatment.

It is known to oxygenate still liquids (i.e., liquids which are substantially gas-free) at super-atmospheric pressure with oxygen from an external source. The impregnation of the liquid with gas is usually carried out in sealed vessels or conduits, with the impregnated liquid subsequentially transferred to bottles or other containers in which it is to be marketed, the bottles filled and sealed under super-atmospheric pressure in order to prevent, so far as possible, the escape of oxygen gas from the liquid. Moreover, it is known to intermix oxygen into liquids by passing the liquid through a venturi mixer or injector and introducing oxygen into the admixture at the venturi throat. Further, it is known that a shockwave may be produced in the diverging outlet of a venturi mixer or injector to promote mixing of the liquid and the gas. Generally, venturi mixers or injectors employed in liquid oxygenating apparatuses are oriented horizontally, or vertically and such that the liquid flow therethrough is upwardly directed.

Currently, one of the most effective known method and apparatus for saturating a liquid with oxygen on an industrial scale is described in published International Patent Application WO 97/27146 and U.S. Pat. No. 5,766,490. According to this process, a sealed enriching space is provided which includes a venturi mixer, through which liquid to be oxygenated upwardly flows, the oxygen gas introduced to the liquid in the venturi throat. This known method and apparatus works well, producing an oxygen-enriched liquid having at least 40 mg/l oxygen at a rate of approximately 50,000 gallons per day (gpd), but does not take full advantage of the mixing potential offered by a venturi mixer or injector. A method and apparatus providing greater oxygen concentrations and flow rates is desirable.

Further, a method and apparatus which can automatically control various aspects of the process of oxygenating a liquid with only the operator's input of a desired, variable oxygen concentration level would be desirable.

SUMMARY OF THE INVENTION

Throughout the specification, drawings and the claims, "water" is meant to include any still or effervescent liquid intended to be enriched with oxygen, and "liquid" is meant to include water and any other still or effervescent liquid that is capable of super oxygenation, including flavored water and other ingestive beverages.

Objects of the present invention include enabling the production of a liquid enriched with oxygen at higher oxygen concentrations and at higher, industrial scale, continuous production rates than has been possible in the prior art, and providing for the improved utilization of such super-oxygenated liquids. The liquid to be enriched with oxygen may be chilled or at ambient temperatures, with greater concentrations of oxygen achievable in chilled liquids.

Another object of the present invention is to provide improved aerobic, therapeutic and fermentation processes employing liquids highly enriched with oxygen in accordance with the present invention.

It is known in the art that there are three approaches to achieving a process providing mass transfer of gas into a liquid. The first approach is to provide a large liquid-gas boundary surface area through which the gas may be absorbed into the liquid. The second approach is to provide a driving force between the gas and liquid phases; the magnitude of the driving force directly correlating with the mass transfer rate, which is directly related to the pressure at the liquid-gas interface. The third approach is to increase the mass transfer coefficient by increasing the relative velocity between the interfacing gas and liquid phases, and the turbulent mixing in the liquid phase. These three approaches are combined in the present invention.

The present invention provides a means of maximizing the liquid-gas boundary area, the driving force between the liquid and gas phases, and the mass transfer coefficient, as well as increasing the time over which mass transfer may occur. This is accomplished by providing a liquid oxygenating system in which the liquid flows downwardly through a venturi-type injector having an inlet forming a nozzle, a throat adjacent thereto in which oxygen is introduced into admixture with the liquid, and a diverging, first diffuser portion directly below and adjacent to the throat and in which a shockwave is produced. The shockwave creates many fine bubbles thereby increasing the surface area of the liquid-oxygen interface. There is pressure recovery downstream of the shockwave.

The plurality of smaller bubbles proceeds downward with the flowing liquid into a second diffuser/absorber portion in which the pressure of the admixed liquid and oxygen phases is increased further. In the first and second diffuser/absorber portions, the linear pressure gradient normally associated with increasing liquid depth in a static liquid is augmented, providing increases in the pressure of and pressure gradient in the liquid and gas phases higher than would otherwise be experienced. In itself, the augmented pressure increase occurring in the first and second diffuser/absorber portions increases the driving force between the gas and liquid phases, increasing the concentration of oxygen molecules at the liquid-gas interface as well, circumstances which promote high gas-to-liquid mass transfer. Further, however, the increased axial pressure gradient on the oxygen bubbles increases their buoyancy in the liquid, causing some of them to float upwards against the downward liquid flow. The oppositely directed flow of oxygen bubbles and liquid yields a high relative velocity therebetween, which increases the gas-to-liquid mass transfer, promoting their intermixing. The high relative velocity between the oxygen bubbles and the liquid, and the turbulent mixing of the liquid, keeps the liquid molecule concentration gradient high at the liquid-gas interface; the oxygen molecule concentration of a bubble, however, is fixed by the pressure acting thereon. The differences in concentrations between the gas and the liquid at their interface promotes the absorption of the oxygen into the liquid, the gas penetrating the boundary surface between the two phases. Also, the large upwardly floating bubbles are broken up into an even greater plurality of even smaller bubbles, further increasing the surface area of the liquid-oxygen interface. Moreover, the residence time of oxygen bubbles in the liquid is increased by their floating in the liquid in the diffuser/absorber, allowing greater opportunity for the gas to be absorbed into the liquid.

The cycle of oxygen bubbles being broken up into a greater plurality of smaller bubbles in the first diffuser portion, the bubbles flowing with the downflowing liquid into the second diffuser/absorber portion, wherein their pressure and buoyancy is increased, and the bubbles floating upwards against the downward liquid flow and being broken up into a greater plurality of even smaller bubbles counterbalances any tendency of the bubbles to coalesce.

The oxygen enriched liquid leaving the second diffuser/absorber portion enters the inlet of an adjacent pipe absorber where, under an approximately constant pressure approximately equivalent to that of the second diffuser/absorber portion outlet, residence time is further provided for the oxygen to even more fully enter solution, the driving force provided essentially by the pressure acting on the admixture. In the pipe absorber, although high oxygen molecule concentrations are present, mixing occurs on a lesser scale because there is a smaller relative velocity between the liquid and the oxygen bubbles therein. In the pipe absorber, mass transfer is primarily accomplished by absorption under pressure, turbulent liquid mixing and high interfacial surface area. To promote further mixing in or following the pipe absorber, however, turbulent mixers may be additionally provided. As used throughout the specification and the claims, "turbulent mixer" means a device, usually comprising vanes or other flow-directing elements for causing turbulent mixing in the absorber to create a mixing effect in liquid flowing therethrough. A turbulent mixer can suitably be a static mixer, in which the flow directing elements are in a stationary or fixed position, or a dynamic mixer, in which some or all of the flow directing elements can either freely rotate, or be rotated by a drive to intensify the mixing effect. Also, the pipe absorber may have various configurations, such as straight and vertical or serpentine, as described further herein below, with longer pipe absorbers providing increased residence time and greater opportunity for absorption under pressure to occur.

The present invention provides an apparatus for oxygenating a liquid, including a liquid pump, supply piping having an inlet connected to the pump outlet and an outlet connected to the liquid inlet of an injector. The liquid inlet of the injector converges to form a nozzle which increases the velocity and reduces the pressure of flow through a throat of the injector, located between the liquid inlet and a liquid outlet. An oxygen inlet is provided in the throat. The injector is arranged such that the injector liquid inlet is above the injector liquid outlet. The apparatus further includes a first diffuser having an inlet connected to the injector liquid outlet, adjacent to the throat, an outlet located below the inlet and a diverging inside surface. The liquid inlet, throat with oxygen inlet and first diffuser having an outlet may comprise a venturi injector. The apparatus further includes a second diffuser having an inlet, an outlet below the inlet and a diverging inside surface. The second diffuser outlet is larger than, and the second diffuser inlet is in fluid communication with, the first diffuser outlet. Liquid is conducted from the pump through the supply piping and downward through the injector and first diffuser to the second diffuser. The apparatus may further include another absorber having an inlet connected to the outlet of the second diffuser. Also, the first and second diffusers may comprise a single diffuser.

The present invention also provides an apparatus for oxygenating a liquid, including a liquid pump, supply piping having an inlet connected to the pump outlet and an outlet connected to the liquid inlet of an injector. The liquid inlet of the injector converses to form a nozzle which increases the velocity and reduces the pressure of flow through a throat of the injector, located between the liquid inlet and a liquid outlet. An oxygen inlet is provided in the throat. The injector is arranged such that the injector liquid inlet is above the injector liquid outlet. The apparatus further includes a first diffuser having an inlet connected to the injector liquid outlet, adjacent to the throat, an outlet located below the inlet and a diverging inside surface. The liquid inlet, throat with oxygen inlet and first diffuser having an outlet may comprise a venturi injector. The apparatus further includes an absorber having an inlet and an outlet, the absorber inlet in fluid communication with the first diffuser outlet, and an injector bypass adapted to conduct a portion of the liquid conveyed through the supply piping around the injector. The bypassed liquid portion is mixed with oxygenated liquid from the injector at a point downstream of the injector. The throughput flow capacity of the apparatus may thus be varied by diverting a portion of the liquid flow from flowing through the injector, that portion instead conducted through the injector bypass.

The present invention also provides a process for enriching a liquid with oxygen, which comprises the steps of: (a) introducing a liquid under pressure into an injector and flowing the liquid downwardly through the injector at a selected liquid volume flow rate: (b) introducing oxygen into the liquid as it flows through the injector to create an admixture of liquid and a first plurality of large oxygen bubbles; (c) introducing the admixture of liquid and first plurality of large oxygen bubbles from the injector downwardly into an upper diffuser portion at such velocity as to create a shockwave therein; (d) breaking the first plurality of oxygen bubbles up into a second plurality of smaller oxygen bubbles with the shockwave, the second plurality greater than the first plurality, thereby increasing the total surface area between the oxygen bubbles and the liquid; (e) increasing the pressure of an admixture of liquid and the second plurality of smaller bubbles in the upper diffuser portion, wherein the buoyancy of smaller bubbles is increased; (f) introducing the admixture into a lower diffuser portion, wherein the pressure of the admixture of liquid and the second plurality of smaller bubbles is further increased, further increasing the buoyancy of the smaller oxygen bubbles; (g) floating at least some of the second plurality of smaller bubbles upwardly against the downward flow of liquid to be broken up by fluid turbulence or contact with the shockwave; (h) continuing the steps (d) through (g) to continually reduce the size and increase the number of the respective bubbles until the bubbles flow with the downwardly flowing liquid from the lower diffuser portion; (i) flowing an admixture of liquid and oxygen bubbles downwardly from the lower diffuser portion; and (j) recovering the oxygen enriched liquid.

The present invention also involves processes for using oxygen enriched liquid prepared in accordance with the preparatory process of the present invention and by the use of the apparatus of the invention. These processes of use include aerobic, disinfection, therapeutic and fermentation processes advantageously employing oxygen-containing liquids. As used throughout the specification and the claims, reference to an "aerobic" process generally includes all chemical and microbiological processes in which a chemical or microbiological process is carried out or is promoted in a liquid medium in the presence of oxygen. "Therapeutic" processes, as used throughout the specification and the claims, involve the oxygenation of the body or its parts by treatment with an agent in a liquid vehicle containing dissolved oxygen. The inventive fermentation processes are those which involve fermenting a fermentation liquor which comprises the oxygen enriched liquid prepared by the inventive apparatus and/or process. Examples of applications employing such fermentation processes include drug production or food processing by microorganisms.

Suitable aerobic processes in which a liquid oxygenated in accordance with the present invention can be advantageously employed include, for example, processes in which heretofore water has been aerated such as by bubbling air thereinto, and also in situ or ex situ bioremediation of contaminated (e.g., with petroleum products) surface and ground waters; wastewater, sludge and animal waste treatment, both by fixed film and by suspended growth methods; rehabilitation of atrophying lakes; biological oxygen demand (BOD) reduction techniques; fresh water aquaculture (e.g., fish farming); salt water aquaculture (e.g., shrimp farming); hydroponic agriculture; odor suppression barriers for anaerobic processes; and insolubilization of dissolved contaminates (e.g., iron, and manganese ions) for removal by filtration or sedimentation. The process of the present invention virtually eliminates any dissolved oxygen deficiencies for most bioremediation and other aerobic processes, thereby substantially reducing the time and cost of effective site treatment.

Microorganisms such as bacteria consume massive quantities of oxygen in the process of assimilating or breaking down waste, and may rapidly deplete the oxygen levels in a biomass. The rate at which oxygen can be introduced into the biomass is a substantial limiting factor on how quickly a breakdown by oxygenation can be achieved, and it is believed that the oxygen levels in the biomass should not exceed the amount which the bacteria can usefully consume without becoming oxidized and killed. The infusion of an oxygen-enriched liquid with dissolved oxygen concentration levels of up to 160 mg/l into a biomass, wherein it may be properly diluted to provide oxygen to the bacteria at its most efficient consumption rate, would allow a more efficient and more rapid aerobic treatment of the biomass, compared to treatments available through use of previous apparatuses and processes, which produce oxygen enriched waters having significantly lower dissolved oxygen concentrations.

Suitable disinfection processes in which a liquid oxygenated in accordance with the present invention can be advantageously employed include, for example, processes wherein a very high level of dissolved oxygen serves to kill microbial life in the same manner as does chlorine or ozone. These oxygen concentration levels would exceed those resulting after dilution in a biomass for aerobic treatment thereof as described above. Without wishing to limit such a disinfection process to these circumstances, it was found that bacteria in a petri dish was killed when merely subjected to oxygen-enriched water prepared according to the present invention and having a dissolved oxygen level of about 50 to 70 mg/l. It is envisioned that a disinfection process employing an oxygen-enriched liquid prepared according to the present invention may involve subjecting certain microbial life to a disinfectant comprising this liquid or, alternatively, oxygenating a liquid contaminated with microbial life according to the present invention, whereby the disinfection would take place during the inventive process.

Suitable therapeutic processes in which a liquid oxygenated in accordance with the present invention can be advantageously employed include, for example, processes for increasing the oxygen content of blood and tissues; oxygenation of wounds to increase the rate of healing and to reduce infections; oxygenated organ transplant storage media; tumor oxygenation for radiation therapy and chemotherapy; lung bypass by oxygenated liquids in case of pulmonary deficiencies; treatment for carbon monoxide poisoning; mouthwashes, dentifrices; topical, including cosmetic treatment media; contact lens treating solutions; and cell level therapeutic applications. Another feature of the present invention is that such oxygenated liquids can be advantageously employed as solvents for physiological saline isotonic solutions, especially when kept in sealed, sterile containers.

If desired, liquids treated in accordance with the present invention can also be made effervescent by the addition of a gas such as carbon dioxide. If carbon dioxide is added after the dissolution of the oxygen in the water, then it will displace a portion of the dissolved oxygen. It has been found, however, that an effervescent liquid can be further enriched with oxygen to a substantial degree after the addition of the carbon dioxide. Even more oxygen can be dissolved in the liquid if the liquid being enriched with the oxygen is chilled at the time of the oxygen enrichment. To an even greater extent than achievable by chilling the liquid, the solubility of oxygen in a liquid may be increased by increasing the pressure of the liquid and oxygen admixture.

With no bypass of liquid around the injector provided and with a vertical pipe absorber approximately 6 feet long employed, the apparatus and process of an embodiment of the present invention rapidly infuses water with dissolved oxygen to levels of approximately 160 mg/l at a flow rate of approximately 100,000 gpd. It was found that an oxygen concentration of the water leaving the second diffuser/absorber portion was approximately 80 mg/l; the additional increase in concentration of 80 mg/l was achieved in the pipe absorber, at a pressure of about 40 psig. It can be understood from these results that a pipe absorber is not necessary to achieve oxygen concentrations of approximately 80 mg/l, and expected that a longer pipe absorber will provide oxygen concentrations somewhat higher than 160 mg/l. The oxygen concentrations in the oxygenated water prepared in accordance with the present invention were measured with a Model No. 32-275-6201 dissolved oxygen sensor and Model No. 31-170-3211 dissolved oxygen analyzer, manufactured by Mettler-Toledo International, Inc. and distributed by Valley Instrument Company.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 2A is a fragmentary, partial sectional side view of a first injector and pipe absorber configuration according to the present invention;

FIG. 2B is a fragmentary, sectional side view of the configuration shown in FIG. 2A, showing turbulent mixers in the pipe absorber;

FIG. 3 is a fragmentary, partial sectional side view of a second injector and pipe absorber configuration according to a further embodiment of the present invention;

FIG. 5 is a fragmentary sectional side view of the second diffuser/absorber portion of FIGS. 2 or 3, showing undesirable backflow therein resulting from its divergence angle $\phi 2$ being too high.

FIG. 6A is a fragmentary, partial sectional side view of a third injector and pipe absorber configuration according to yet another embodiment of the present invention;

FIG. 6B is a partial side view of the configuration shown in FIG. 6A, showing a serpentine pipe absorber;

FIG. 7 is an enlarged fragmentary sectional side view of the injector and diffuser of the third configuration of the present invention shown in FIG. 6A and 6B;

FIG. 8 is a schematic drawing of an alternative oxygenating apparatus according to the present invention, showing an injector bypass used with the third configuration of the injector and diffuser shown in FIGS. 6A and 6B;

Figure 1:
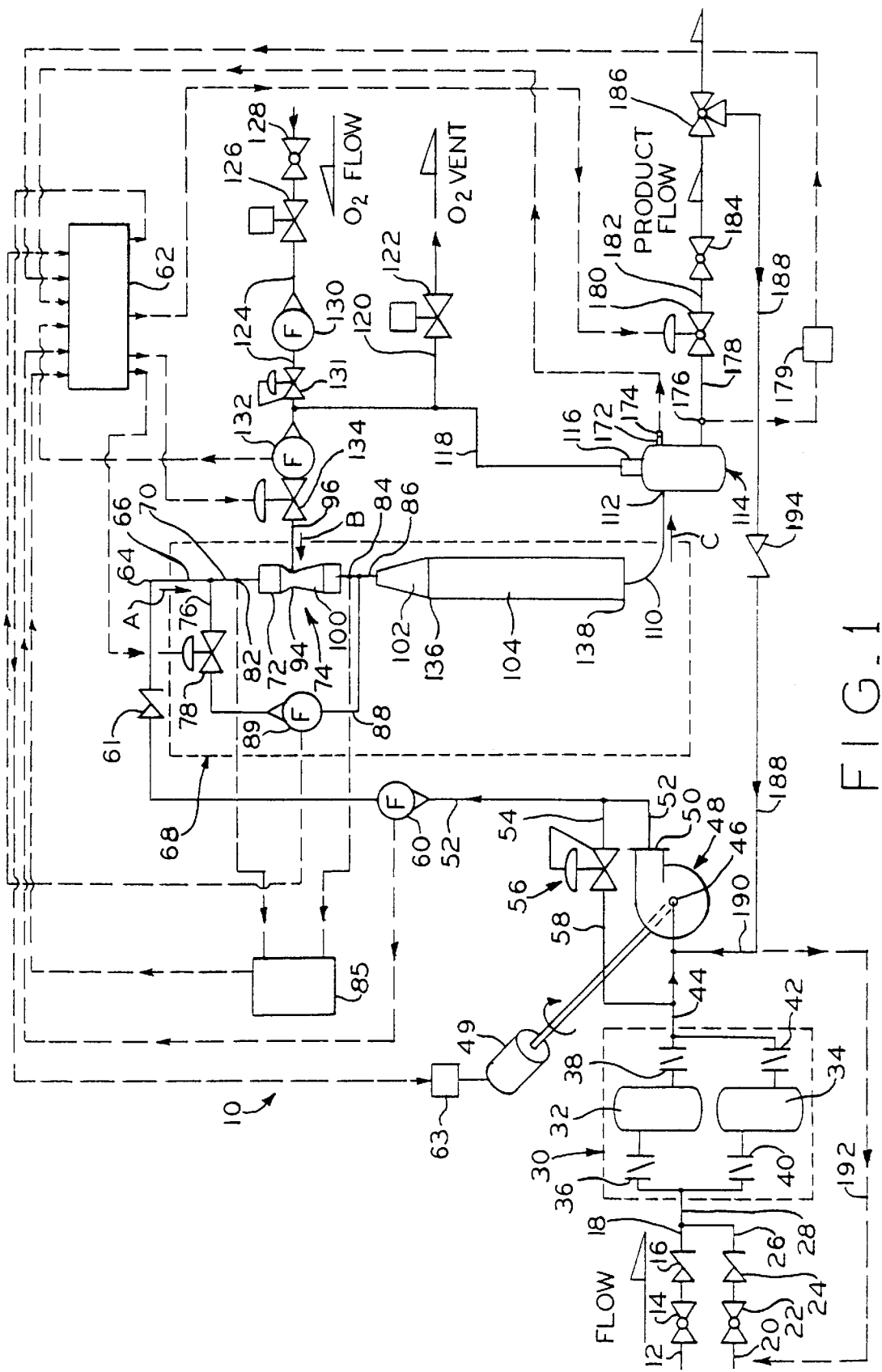
FIG. 1 is a schematic drawing of an oxygenating apparatus according to an embodiment of the present invention, showing a first injector bypass and absorber configuration.

Corresponding reference characters indicate corresponding parts throughout the several views. Although the drawings represent embodiments of the present invention, the drawings are not necessarily to scale and certain features may be exaggerated in order to better illustrate and explain the present invention. The exemplifications set out herein illustrate embodiments of the invention in alternative forms, and such exemplifications are not to be construed as being exhaustive or to limit the scope of the invention in any manner.

DETAILED DESCRIPTION OF THE INVENTION

Referring to the drawings and particularly to FIG. 1, there is shown oxygenating apparatus 10 according to the present invention. As seen at the left side of this figure, a first liquid to be oxygenated, which may be water or another liquid susceptible to super oxygenation, is introduced into the apparatus through supply line 12 which is connected to valve 14. Flow of the first liquid continues from valve 14 through check valve 16 and into pipe portion 18. Alternatively, a second liquid, which may be different from the first liquid, the same as the first liquid but from a separate source or recycled oxygenated liquid from the outlet of apparatus 10, may be introduced (or reintroduced, in the case of a recycled oxygenated liquid) into apparatus 10 through supply line 20 and through its associated valve 22 and check valve 24 into pipe portion 26. In the shown embodiment, pipe portions 18 and 26 are fluidly connected to common pipe portion 28 which is connected to the inlet of duplex filter 30, represented by the ghosted rectangle indicated with that reference numeral. In the shown embodiment, the second liquid, if any, entering apparatus 10 through supply line 20, may be mixed with the first liquid at the juncture of pipe portions 18 and 26 prior to the mixture being filtered. Alternatively, only the second liquid may be introduced (or reintroduced) into apparatus 10. Pipe portions 18, 26 and 28 may be 3 inch schedule 40 pipe having smooth interior walls. To suit most applications, pipe portions 18, 26, 28 and all other pipe portions comprising apparatus 10 may be stainless steel. Other common pipe materials, including PVC, carbon steel, lead, copper, and the like, may instead be used if the pipe material will not be adversely affected by, or adversely affect, the liquid(s) flowing therethrough in normal or oxygen enriched states. Pipe dimensions, unless otherwise specified, refer to its standard diametrical size, not its length. Also, pipe schedules may range, in the shown embodiments, from 40 down to 10.

Duplex filter 30, which may be Tate Andale Model DU-200-304SS, comprises first filter 32 and second filter 34 arranged in a parallel flow configuration. Butterfly valves 36 and 38 are provided in fluid conduits leading to and from first filter 32, and butterfly valves 40 and 42 are similarly provided in fluid conduits leading to and from second filter 34. Valves 36 and 38 are manually closed or opened together, while valves 40 and 42 are manually opened or closed together. The pair of valves 36, 38 are open only when the pair of valves 40, 42 are closed, and conversely. By this arrangement first filter 32 may be serviced without interrupting the flow of liquid into apparatus 10, the flow being directed through second filter 34. Similarly, second filter 34 may be serviced by closing valves 40 and 42, while valves 36 and 38 remain open, the flow of liquid into apparatus 10 being filtered through first filter 32. Those skilled in the art will appreciate that the operation of valve pairs 36, 38 and 40, 42 may be automated.

The filtered liquid flows from duplex filter 30 through 2½ inch pipe portion 44 to inlet 46 of pump 48 having variable speed drive motor 49. Pump 48 may have a flow capacity of 140 gallons per minute (gpm) at 125 psig, and may be 20 hp Gould Model 5SVB1N5E0. So equipped, apparatus 10 provides a minimum flow rate of approximately 72 gpm or about 103,400 gpd, and a maximum liquid flow rate of approximately 139 gpm or about 201,600 gpd.

Downstream of pump outlet 50 and in fluid communication with 2 inch pipe portion 52 connected thereto, is 2 inch pipe portion 54 which leads to the inlet of self-regulating valve 56. Self-regulating valve 56 monitors the fluid pressure at its inlet, and is normally closed. When fluid pressure in pipe portion 54 exceeds 125 psig, however, liquid flow is directed from pipe portion 52 through pipe portion 54 and valve 56 into 2 inch pipe portion 58, which is fluidly connected with pipe portion 44 at a point intermediate duplex filter 30 and pump inlet 46. Flow through pipe portion 58 is recirculated through pump 48 and is prevented from back flowing into supply lines 12, 20 by check valves 16, 24. Thus, self-regulating valve 56 alleviates overly high liquid pressures within the apparatus by recirculating the liquid through the pump rather than causing the pump to continually force liquid at overly high pressure and low flow into apparatus 10. A switch (not shown) may be provided in pipe portion 58 which detects appreciable flow through self-regulating valve 56 and causes the system to shut down rather than recirculate liquid through the pump for a prolonged period.

Pipe portion 52 is provided with magnetic flow meter 60 and check valve 61. Magnetic flow meter 60 provides an electrical signal corresponding to the liquid flow therethrough to controller 62 which, in turn generates a control signal to variable speed drive (VSD) controller 63 of pump motor 49. Pipe portion 52 reaches a maximum height at point 64, after which the liquid flows downwardly through the injector and absorber as described further below. In a prototype of apparatus 10 adaptable to accommodate each injector/diffuser/absorber configuration described herein below, pipe portion 52 reaches a maximum height of approximately 17 feet above floor level.

Connected to pipe portion 52 at point 64 is vertical 3 inch pipe portion 66 which conducts liquid in a downward direction as indicated by arrow A. The downward flow of liquid to be oxygenated along the path indicated by arrow A is common to the various injector/diffuser/absorber configurations described further below. Apparatus 10 may be schematically adapted to integrate each of these injector/diffuser/absorber configurations by interchanging them within ghosted rectangle 68 of FIG. 1, which shows an embodiment of apparatus 10 with a first injector/diffuser/absorber configuration. Further, as will be discussed further below, oxygen is introduced into the injector of each injector/diffuser/absorber configuration, and schematically into ghosted rectangle 68, along the path indicated by arrow B. Oxygenated liquid exits the pipe absorber of each injector/diffuser/absorber configuration, and schematically from ghosted rectangle 68, along the path indicated by arrow C.

As shown in ghosted rectangle 68 of FIG. 1, one embodiment of apparatus 10 includes a first injector/diffuser/absorber configuration according to the present invention. This first configuration includes vertical reducer pipe portion 70 connected to the outlet of pipe portion 66 and which continues the flow of liquid in a downward direction towards the injector inlet. Reducer pipe portion 70 has a frustoconical inner surface communicating its upwardly directed inlet, having a diameter of approximately 3 inches, with its downwardly directed outlet, having a diameter of approximately 1½ inches. The included angle between radially opposite walls of reducer 70 is between approximately 15° and 20°. The outlet of reducer 70 is connected to liquid inlet 72 of injector 74. The first injector/diffuser/absorber configuration further comprises 2 inch outside diameter stainless steel tube portion 76 which is teed into the connection between pipe portion 66 and reducer 70 and leads to the inlet of bypass valve 78. Bypass valve 78, which may be Bauman Model 70-24577S, is automatically adjusted in response to an electrical signal issued by controller 62 based on a pressure differential sensed between pressure taps 82 and 84 on opposite sides of the injector, or may be controlled by an overriding signal generated from controller 62 based on the operator's input. Differential pressure transmitter 85 is fluidly connected to pressure taps 82, 84 via an intervening strain gauge diaphragm, each side of which is exposed to fluid pressure. The varying resistance across the strain gauge produces a varying voltage signal read by transmitter 85, which generates an amplified electrical signal proportional thereto which is transmitted to controller 62. Controller 62 uses a proportional integral algorithm to generate an electrical signal which is transmitted to valve 78. An external source of regulated, compressed air (not shown) is provided to valve 78, which is provided with an electropneumatic transducer which receives the electrical signal from controller 62 and converts it to a proportional air pressure which effects the actuation of the liquid valve. Alternatively, valve 78 may be of a type which is actuated electromechanically, without utilizing air pressure. Pressure tap 82 is located upstream of injector 74, in reducer 70, and pressure tap 84 is located downstream of injector 74, in cylindrical conduit element 86, which is described further below.

Figure 4:
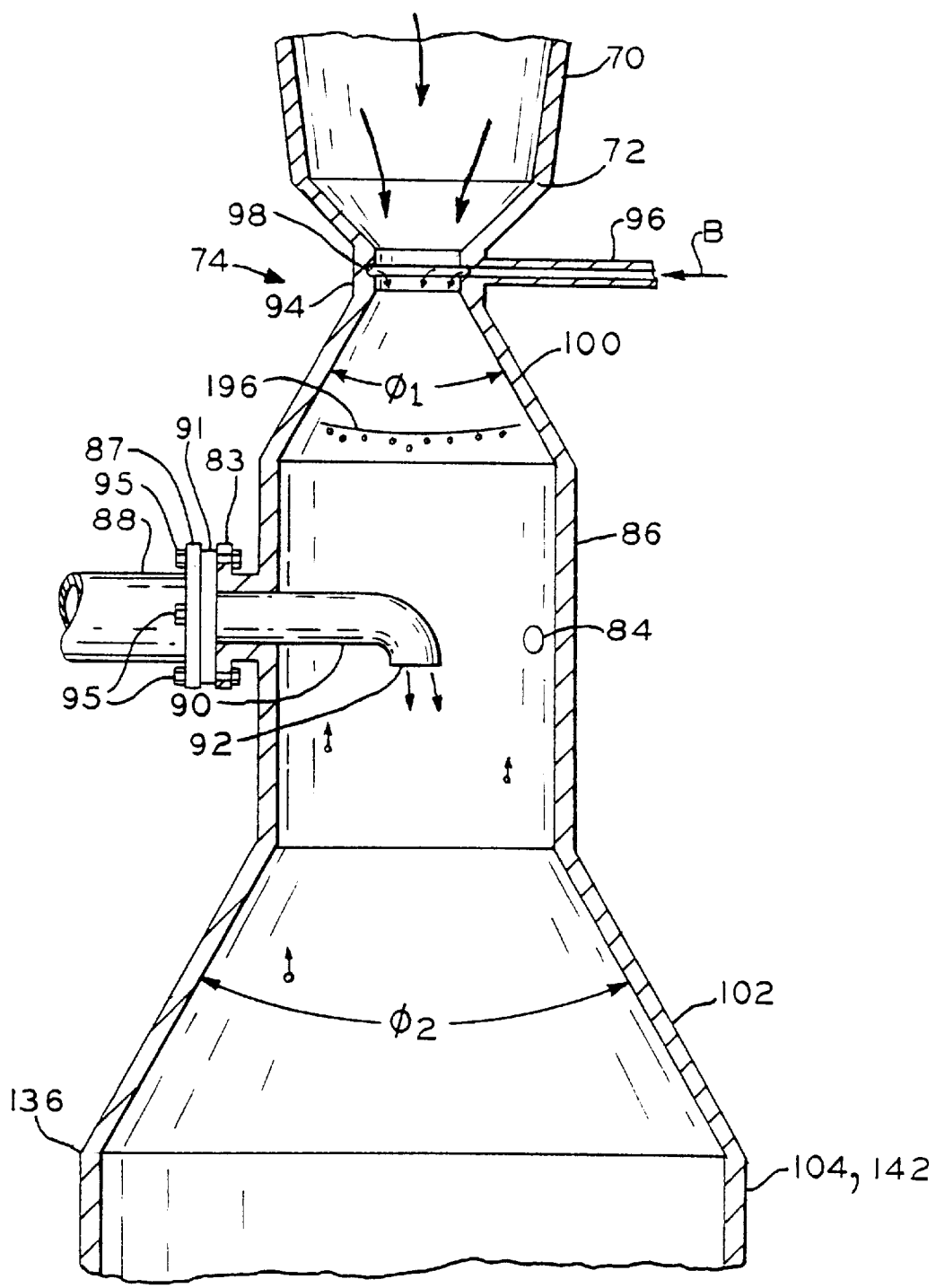
FIG. 4 is an enlarged fragmentary sectional side view of the injector, diffuser and injector bypass of the first and second configurations of the present invention shown in FIG. 2, also showing a shockwave formed in the first diffuser portion.

Valve 78 allows a portion of the high pressure liquid flowing downward through pipe portion 66 to be diverted through tube portion 76 to tube 88 connected to the valve outlet. Tube portion 88, like tube portion 76, is constructed of 2 inch outside diameter schedule 10 stainless steel tubing, although each of tube portions 76, 88 may be of any suitable material. Tube portion 88 is provided with magnetic flow meter 89 which provides an electrical signal corresponding to the liquid flow therethrough to controller 62. Controller 62 compares the outputs of flow meters 60 and 89 and provides indicia, such as a displayed value, of the difference, which represents the liquid flow through injector 74. In the first and second injector/diffuser/absorber configurations, shown in FIGS. 2 and 3, tube portions 76, 88 and valve 78 comprise an injector bypass. Liquid flowing through the injector bypass is directed around, rather than through, injector 74 and is introduced into the stream of oxygenated liquid downstream thereof, reentering the flow of oxygenated liquid in cylindrical conduit element 86 intermediate the first and second diffuser portions, as will be discussed further below. Conduit element 86 may be a 2 inch schedule 40 stainless steel pipe portion. As best seen in FIG. 4, nozzle 90, comprising a 90 degree, 1 inch outside diameter tube, is attached to flange 91 which is held in place between flange 87 on 2 inch outside diameter tube portion 88 and flange 83 provided on element 86, and is in fluid communication with tube portion 88. Flanges 83, 87 and 91 are attached together with bolts 95. Downwardly directed outlet 92 of nozzle 90 is centrally located within conduit element 86; liquid flowing downward from injector 74 flows past nozzle 90 in approximately surrounding fashion and mixes with the downward flow of injector-bypassing liquid from nozzle outlet 92. The output flow capacity of embodiments of apparatus 10 having first or second injector/diffuser/absorber configurations, further described below, may be increased from approximately 100,000 gpd to approximately 200,000 gpd by providing liquid flow through the above-described injector bypass, although diluted product liquid concentrations will result.

As shown in FIG. 2A, liquid to be oxygenated flows downwardly through reducer 70 into liquid inlet 72 of injector 74. Liquid inlet 72 is configured to provide a nozzle which increases the speed and reduces the pressure of the liquid flowing through the injector. The outlet of the injector liquid inlet nozzle has a diameter of about 0.5 inch, and is immediately adjacent and upstream of cylindrical injector throat 94, also of about 0.5 inch diameter. Oxygen is introduced into injector 74 from oxygen supply tube 96 and is mixed with the liquid flowing through injector 74 at throat 94. Referring now to FIG. 4, injector throat 94 is provided with annular groove 98 in its interior, cylindrical surface. Oxygen supply tube 96, through which oxygen is provided in the direction indicated by arrow B to injector 74, is in fluid communication with groove 98 and introduces the oxygen to the liquid flowing through throat 94 in a surrounding fashion, after which they are mixed. Immediately adjacent and downstream of the outlet of throat 94 is the inlet of first diffuser portion 100. Injector 74 may be a venturi injector of the type manufactured by Mazzei Injector Corporation as Model 1584-A, which includes integral liquid inlet 72, throat 94 and first diffuser portion 100. Alternatively, injector 74 may be comprised of individual liquid inlet, oxygen inlet/throat and first diffuser portion components. Liquid flow through the Mazzei Model 1584-A venturi injector is limited to a maximum of approximately 100,000 gpd. First diffuser portion 100 is frustoconical and divergently opens downwardly at included angle φ1 from its inlet, having inner diameter of approximately 0.5 inch, to its outlet, having an inner diameter of approximately 1.13 inches. Included divergence angle φ1 between radially opposite inner walls of first diffuser portion 100 is in the range between approximately 8° and 10°, with a taller diffuser having a smaller angle φ1 preferable to a shorter, more rapidly diverging diffuser. A conical adapter (not shown) fluidly communicates the outlet of first diffuser portion 100 to the 1.870 inch inner diameter inlet of cylindrical conduit element 86.

The inner diameter of cylindrical conduit element 86 is equivalent to the inner diameter of the inlet to second diffuser/absorber portion 102, through which liquid downwardly-flows from element 86. Second diffuser/absorber portion 102 is generally frustoconical and divergently opens downwardly at included angle φ2 between its radially opposite inner walls from its inlet, having an inner diameter of approximately 1.870 inches, to its outlet, having an inner diameter of approximately 4 inches, matching the inner diameter of the adjacent inlet of cylindrical pipe absorber 104. Included divergence angle φ2 is in the range between approximately 8° and 10°, with a taller diffuser/absorber having a smaller angle φ2 preferable. Angles φ1 and φ2 may be equivalent.

Backflow and/or turbulence in diffuser/absorber portion 102, which may be manifested by vortices produced near the inside surface thereof, are undesirable. Referring to FIG. 5, if divergence angle φ2 is too great, backflow, represented by arrows D, may occur in region 106 inside second diffuser/absorber portion 102 downstream of transition point 108 where the flow separates from the frustoconical interior wall surface, adversely influencing the ability of second diffuser/absorber portion 102 to raise the pressure of the fluid and increase the buoyancy of the oxygen bubbles therein, the significance of which was earlier mentioned and will be discussed further below. Hence, a taller second diffuser/absorber portion having a smaller divergence angle φ2 is preferable to a shorter diffuser portion having a larger divergence angle.

In each of the three injector/diffuser/absorber configurations, oxygenated liquid exits the pipe absorber through a pipe portion and schematically from ghosted rectangle 68, along the path indicated by arrow C in FIG. 1. As this figure shows, oxygenated liquid flows from the pipe absorber through pipe portion 110 to inlet 112 of gas separator tank 114, wherein oxygen which has not been absorbed into solution with the liquid collects in the upper portion. Oxygen exits gas separator tank 114 through gas relief valve 116, which may be Valmatic Model VC-22, in the top of the separator tank, and enters tube 118 connected to valve 116. Oxygen flowing through tube 118 may then be vented to the atmosphere through tube portion 120 and its associated automatic shutoff valve 122 or, preferably, recycled back to the injector of the apparatus where it can be used in further processing. Tube 118 is thus in fluid communication with oxygen supply tube 124, which is connected through its associated automatic shutoff valve 126 to a oxygen supply valve 128. Automatic shutoff valve 122 is open to vent only during system startup to evacuate all gases from the apparatus prior to system operation. Upstream of its connection to tube 118, oxygen supply tube 124 is provided with oxygen flow meter 130 and self-regulating valve 131, which controls the oxygen pressure at its outlet to a pressure that is less than the minimum operating pressure of gas separator tank 114. Thus, if oxygen accumulates in tank 114 and is relieved by valve 116 into tube 118, it will have a pressure exceeding the pressure setting of self-regulating valve 131 and preferentially flow into total oxygen flowmeter 132 and hence to oxygen supply tube 96. Upstream of tube 118, oxygen supply tube 124 is provided with oxygen mass flow meter 130 for monitoring the flow of supplied oxygen. Flow meter 130 may be Model No. 830-M-4-OV1-SX-D-V1-S0-MP-N800L manufactured by Sierra Instruments. In response to the mass flow of total oxygen as sensed by flow meter 132, controller 62 issues a signal to gas mass flow controller 134, which regulates the supply of oxygen flowing therethrough and which is provided to oxygen tube 96 and injector 74. Flow meter 132 and gas mass flow controller 134 may be combined into a single unit, as in Sierra Instruments Model No. 840-M-4-OV1-SV1-D-V1-S1-N800L-4X. The supply of oxygen to tube 96 and injector 74 is regulated by valve 134 to normally provide oxygen at a pressure between 1 atmosphere and about 30 psig. Generally, for maximum oxygenation, the flow rate of oxygen provided to injector 74 should be at least the amount necessary to completely saturate the quantity of liquid flowing through the injector and may, depending on the liquid and operating conditions of the system, be higher. For example, in one instance of system operation which resulted in 170 mg/l oxygen concentration in water, one embodiment of the present invention called for an oxygen flow rate approximately 67% greater than the amount necessary to completely saturate the quantity of liquid flowing through the injector. Notably, however, the oxygen flow rate may be much greater than required to completely saturate the quantity of liquid flowing through the injector without wasting the oxygen, for it is recycled to the injector as indicated above.

Referring to FIG. 2A the outlet of second diffuser/absorber portion 102 is connected to the inlet of pipe absorber 104 at point 136. The outlet of pipe absorber 104, at point 138, is connected via a curved conduit to the inlet of pipe portion 110. The distance of straight, vertical pipe absorber 104 between points 136 and 138 is approximately 6 feet. Longer lengths may be desirable depending on the time of residency of oxygen bubbles in the admixture, and shorter lengths may also provide adequate performance, depending on the desired level of oxygen concentration in the product liquid. As seen in FIG. 2B, which is identical in all other respects to FIG. 2A, turbulent mixers 140 may be provided in pipe absorber 104 to promote mixing of the oxygen bubbles in the liquid. The liquid/oxygen admixture flows through mixers 140 in pipe absorber 104 along downward and somewhat spiraling paths as indicated by arrows E. Turbulent mixers 140 may be of static type, in which their position is stationary or fixed, or of dynamic type, in which they may rotate freely or by means of a drive mechanism (not shovel).

Referring now to FIG. 3, there is shove a second configuration of the oxygenating apparatus 10 according to the present invention. Upstream of point 136, where the outlet of second diffuser/absorber portion 102 is connected to the inlet of the pipe absorber, the second configuration is essentially identical to the first configuration (FIGS. 2A, 2B), the primary difference being that rather than having a pipe absorber comprising a single, vertically extending portion, pipe absorber 142 having a serpentine configuration is provided. Serpentine pipe absorber 142 comprises a plurality of vertical 4 inch diameter pipe portions 144, 146, 148 connected in series by 180° curved conduit portions 150, 152 of the same diameter.

Curved conduit portions 150, 152 and vertical pipe portions 144, 146 and 148 may be integral; that is, serpentine pipe absorber 142 may be comprised of a single 4 inch diameter pipe providing elongated portions 144, 146 and 148 each of which may be approximately 6 feet long with intermediate bends comprising curved conduits 150, 152. In curved conduit portion 150 is provided manual valve 154 through which vertical pipe portions 144 and 146 may be drained of liquid. Curved conduit portion 152 is provided with manual valve 156 through which gas pockets trapped between vertical pipe portions 146 and 148 may be purged. The outlet of vertical pipe portion 148, at point 138', is connected via a curved conduit to the inlet of pipe portion 110', the outlet of which, as in the first configuration, is connected to inlet 112 of gas separator tank 114, conducting the flow of oxygenated liquid along the path indicated by arrow C (FIG. 1). Also, as shown in FIG. 3, turbulent mixers 140 may be provided in serpentine pipe absorber 142 to promote mixing therein, as described above.

Compared to pipe absorber 104, serpentine pipe absorber 142 provides increased time for the oxygen bubbles to more fully enter solution with the liquid under pressure, the increased residence time providing higher oxygen concentrations in the product liquid. It will be apparent to those skilled in the art that the pipe absorber may be elongated and have shapes other than that of pipe absorber 142. For example, the pipe absorber may instead be formed in a continuous spiral between its inlet and outlet, or comprises a plurality of interconnected straight pipe portions of various lengths. Further, apparatus 10 may be adapted to provide a straight pipe absorber similar to absorber 104 (FIGS. 2A, 2B), but longer.

Referring now to FIGS. 6A an 6B, a third injector/diffuser/absorber configuration of oxygenating apparatus 10 may be seen. As in the first and second injector/diffuser/absorber configurations, liquid to be oxygenated enters pipe portion 66 along the path indicated by arrow A (FIG. 1), and flows through reducer 70' to the liquid inlet of injector 74'. Unlike the first two injector/diffuser/absorber configurations of FIGS. 2 and 3, the third configuration does not provide an injector bypass from a location intermediate pipe portion 66 and reducer 70' to a conduit element intermediate the first and second diffuser portions. Like the first two injector/diffuser/absorber configurations, however, injector 74' of the third configuration may be a venturi injector. For example, injector 74' may be Mazzei Model 2081-A, which has a maximum liquid flow capacity of approximately 190,000 gpd. The outlet of reducer 70' connects with the 2 inch liquid inlet of injector 74', which is provided with a nozzle having an outlet of approximately 0.7 inch. The outlet of the injector liquid inlet nozzle is adjacent and upstream of cylindrical injector throat 94', also of about 0.7 inch diameter. Oxygen is introduced into injector 74' from oxygen supply tube 96 and is mixed with the liquid flowing through the injector at throat 94'. Referring now to FIG. 7, in the manner described above, the oxygen is introduced into annular groove 98' in throat 94' and surrounds the flow of liquid, intermixing therewith. Immediately adjacent and downstream of the outlet of throat 94' is the inlet of first diffuser portion 100'. First diffuser portion 100' is frustoconical and divergently opens downwardly from a diameter of approximately 0.7 inch at its inlet, at included angle φ3 to its outlet, which continues directly into the inlet of second diffuser/absorber portion 102' having preferably identical included divergence angle φ3. Second diffuser/absorber portion 102' has an outlet inner diameter of approximately 4 inches, matching the inner diameter of the pipe absorber inlet to which it is connected at point 136. Included divergence angle φ3 is in the range between approximately 8° to 10°, with a taller first diffuser portion having a smaller angle φ3 preferable. Where Mazzei venturi injector Model 2081-A serves as injector 74', its integral diverging outlet comprises first diffuser portion 100', to which the inlet of second diffuser/absorber portion 102' is immediately adjacently connected, providing a transition between diffuser portions 100' and 102' which is continuous and smooth as possible. As in the case of injector 74, injector 74' may, alternatively, be comprised of individual liquid inlet, oxygen inlet/throat and diffuser components. Where the Mazzei Model 2081-A venturi injector is used, included angle of divergence φ3 between opposite sides of the frustoconical inner walls of both diffuser portions 100' and 102' is approximately 10°. Preferably, however, angle φ3 should be no more than about 8° to better ensure against the formation of backflow region 106 in the diffuser, as discussed above with reference to FIG. 5. It will be apparent to those skilled in the art that diffuser portions 100', 102' need not consist of separable components, but rather may be combined into a single diffuser having an upper portion corresponding to first diffuser portion 100' and a lower portion corresponding to second diffuser/absorber portion 102', the single diffuser having a single frustoconical inner surface with divergence angle φ3 of no more than about 8°.

Referring again to FIGS. 6A, 6B, it is shown that in the third injector/diffuser/absorber configuration, as in the first two configurations, liquid exiting second diffuser/absorber portion 102' is connected at point 136 to the inlet of the pipe absorber. As in the first configuration, pipe absorber 104 may be adapted to connect with the outlet of diffuser/absorber portion 102' or, as in the second configuration, serpentine pipe absorber 142 may be used. Also, as in the first two configurations, the third configuration may use turbulent mixers 140 (FIGS. 2B, 3) in either pipe absorber 104 or 142, the turbulent mixers being of the static or dynamic variety. Further, as in the second configuration, valves 154 and 156 may be provided in curved conduit portions 150 and 152 of serpentine pipe absorber 142. As described above, the outlet of pipe absorber 104 or 142 is connected at point 138, 138' to pipe portion 110, 110', which conducts the oxygenated liquid to inlet 112 of gas separator tank 114, along the path indicated by arrow C.

Referring now to FIG. 8, it may be seen that apparatus 10', comprising the third injector/diffuser/absorber configuration of FIGS. 6A, 6B, is provided with an injector bypass comprising 2 inch outside diameter schedule 10 stainless steel tube portions 158, 160 fluidly connecting pipe portion 52 and inlet 162 of gas separator tank 114', joined by valve 164. Gas separator tank 114' is generally identical to gas separator tan 114 except for being provided with additional liquid inlet 162. Valve 164 is identical to injector bypass valve 78 of the first two injector/diffuser/absorber configurations, and is actuated in response to differences in pressures sensed via pressure taps 82 and 166, in the manner described above for operating valve 78. Pressure tap 166 is located in gas separator tank 114'. Bypass tube portion 158 is provided with magnetic flow meter 168 and check valve 170. Flow meter 168 provides an electrical signal corresponding to the liquid flow therethrough to controller 62. Controller 62 compares the outputs of flow meters 60 and 168 and provides indicia, such as a displayed value, of the difference, which represents the liquid flow through injector 74'. When valve 164 is opened, liquid flows through the injector bypass in the direction indicated by arrow F, providing liquid which has been diverted from passing through injector 74' to gas separator tank 114', where it is mixed with the oxygenated liquid received from the pipe absorber through pipe portion 110 or 110' (FIG. 6B). If Mazzei Model 1584-A is used as injector 74' in apparatus 10', the injector bypass shown in FIG. 8 may approximately double the flow capacity of the apparatus from about 100,000 to 200,000 gpd. If Mazzei Model 2081-A is used as injector 74' in apparatus 10', provided that pump 48 is of sufficient capacity, the injector bypass shown in FIG. 8 may approximately double the flow capacity of the apparatus from a range of about 160,000 to 190,000 gpd to a range of about 320,000 to 380,000 gpd. As with the injector bypass of the first and second configurations, a consequence of the increased output flow capacity achieved with the injector bypass shown in FIG. 8 is a reduced oxygen concentration in the product liquid. Notably, the point at which an injector bypass introduces bypassed liquid to the admixture stream may be other than as described above. For example, bypassed liquid may be introduced to the admixture stream between the second diffuser/absorber portion and the pipe absorber, thus providing an opportunity for oxygen molecules to enter solution with the unenriched, bypassed liquid in the pipe absorber.

Gas separator tanks 114 (FIG. 1) and 114' (FIG. 8) are provided with fitting 172 at which the liquid discharge pressure in the tank may be sensed by transducer 174, which provides an electrical signal corresponding to the tank's liquid pressure to controller 62. Dissolved oxygen sensor 176 is provided in pipe portion 178 which leads from tank 114, 114' to valve 180. Sensor 176, which may be of the type manufactured by Ingold Mettler-Toledo, Inc. as Model 32-275-6201, in conjunction with dissolved oxygen analyzer 179, which may be of the type manufactured by Ingold Mettler-Toledo, Inc. as Model 31-170-3211, provides an electrical signal corresponding to the sensed level of dissolved oxygen in the product liquid to controller 62. Controller 62, in response to the electrical signals associated with transducer 174 and sensor 176, generates an electrical signal to valve S80, interconnected between pipe portion 178 and pipe portion 182, which regulates the pressure of liquid flowing through apparatus 10, 10' by restricting the flow of oxygenated liquid therethrough, but does not completely close during operation of the apparatus. Valve 180 may be Fisher Series V200, Model 317SS, which operates in the same way valve 78 does, converting the electrical signal received from controller 62 into a pneumatic pressure for mechanical valve actuation. Alternatively, valve 180 may be of a type which is actuated electromechanically without utilizing air pressure. During operation of the apparatus, adjustment of valve 180 regulates the pipe absorber pressure and, consequently, the injector liquid inlet pressure, which, given the flow capacity of the apparatus and an oxygen level of at least 150 mg/l in water, are normally between approximately 40 to 50 psig and 80 to 90 psig, respectively. These pressures may be lower for lower flow capacities and/or dissolved oxygen concentration levels. In the automated control of valve 180, if the dissolved oxygen level sensed by sensor 176 exceeds the oxygen concentration set point, the valve is opened at a rate corresponding to the sensed oxygen overage, reducing the liquid pressure in the apparatus, which is in turn sensed by transducer 174. Should the sensed pressure fall below, for example, approximately 40 psig, controller 62 will begin to close valve 180, ensuring second diffuser/absorber portion 102, 102' pressure, which is approximately equivalent to that sensed in tank 114, 114', is maintained at least at the minimum pressure necessary to properly perform the oxygenation process.

Should the dissolved oxygen level sensed by sensor 176 fall below the oxygen concentration set point, valve 180 is closed at a rate corresponding to the sensed oxygen deficiency, increasing the liquid pressure in the apparatus, which is in turn sensed by transducer 174. Should the sensed pressure increase beyond, for example, approximately 90 psig, controller 62 will begin to open valve 180, ensuring second diffuser/absorber portion 102, 102' pressure, which is approximately equivalent to that sensed in tank 114, 114', is low enough to maintain flow through the apparatus. Sensor 176 is slow to respond to changes in oxygen concentration; therefore transducer 174 is provided to generate the signals necessary to limit the operation of valve 180 to ensure the process properly continues. Further, should the pressure sensed by transducer 174 rise above or fall below programmed operating limits, irrespective of whether a change is sensed in oxy,en concentration, controller 62 will accordingly adjust valve 180. Thus, the system may be controlled without sensor 176.

Connected to the end of pipe portion 182 opposite the end connected to valve 180 is valve 184, from which the final oxygenated liquid product is recovered from apparatus 10, 10' for its use. Recovery of the final product may be made under pressure, as when filling vessels to be sealed for shipment and storage. Valve 184 should be open at all times while the oxygenating apparatus is operating, but may be closed to isolate apparatus 10, 10' without its being drained should downstream facilities require disconnection therefrom.

Downstream of valve 184, 3-way valve 186 may be provided for recirculating oxygenated liquid back to apparatus 10, 10' via pipe portions 188, 190 to pipe portion 44, upstream of pump inlet 46. Alternatively, the recirculated liquid may be conveyed to the inlet of valve 22 via pipe portions 188, 192, the recirculated liquid comprising the above mentioned second liquid supplied to apparatus 10, 10'. Pipe portion 188 may be provided with check valve 194 to ensure proper flow direction therethrough.

Controller 62 may be an Allen-Bradley Model PLC-5 programmable logic controller (PLC) comprising a rack, controller with firmware, a power supply and input/output modules. The PLC-5 controller's firmware is provided with canned proportional, integral and derivative (PID) calculation algorithms, as commonly used in fluid process control systems. As described further below, based on the differential between the received signals corresponding to the measured value and the setpoint, the PID algorithms arrive at an output value for adjusting the process control devices described above (i.e., pump motor 49 and control valves 78, 134, 164 and 180) through comparison of one or more input signals received by PLC controller 62 with a corresponding desired, setpoint value.

As described farther below, some of the control loops, comprising the sensing device, controller 62 and the PID algorithm, and the process control device, are provided with "Remote/Local" switches to allow the controller to receive the setpoint from either a manual input at the man/machine interface (MMI, not shown) in the Local mode position, or from an electronic or software source in the Remote mode position. Controller 62 is adapted to provide either local or remote setpoint input to all control loops having remote/local switches. Further, certain control loops are individually provided with "Manual/Auto" switches in the system software which allow apparatus 10, 10' to be directly commanded either by a manual input at the MMI in the Manual mode position, or by the PID algorithm output controller 62 in the Auto mode position. Certain of the control loops are also individually provided with "Startup (SU)/Normal" (or a "Startup (SU)/Shutdown (SD)/Normal") logical switch in the system software which allow controller 62 to take direct control of process control devices in apparatus 10, 10' during automatic startup and shutdown sequences. In conjunction with a "Unit Running" on/off logical switch (not shown), the Startup/Normal switches dictate the system operating mode of the apparatus in the following manner. If the Unit Running switch is off and the Startup switch is also off, the apparatus is off. If the Unit Running switch is on and the Startup switch is also on, the apparatus is in startup mode. If the Unit Running switch is on and the Startup switch is off, then the apparatus is in its normal, running mode. If the Unit Running switch is off and the Startup/Shutdown switch is on, then the apparatus is in its shutdown mode.

The startup sequence determines for each loop when it can operate in a normal mode; the shut down sequence determines for each loop when it must take over control of the corresponding process control device. FIGS. 9A–9E show schematically, how each of the above-described control loops are basically configured in controller 62, wherein these figures the comparison of the input signal(s) received by controller 62 with the corresponding setpoint value is represented by $\Delta$. The automatic system controls are farther described with individual emphasis on analog control loops, analog monitoring and discrete control logic. The analog control loops of the automatic system controls, shown in FIGS. 9A–9E, take values such as process measurements or setpoints and generate outputs based on these values. The output of a control loop may control a device such as a valve or the pump, or may provide a setpoint for another control loop. In the apparatus of the present invention, analog transmitters deliver signals to PLC 62, which performs PID control algorithms to generate the output values. As seen in FIGS. 9A–9E, the control loops have the following modes: Manual mode, in which the output is controlled directly by the operator; Local Auto mode, in which the output is determined by the PID algorithm using a process setpoint entered by the operator; and Remote Auto mode, in which the output is determined by the PID algorithm using a process setpoint set by an analog input or an internally calculated value, such as another control loop. In the control of the present invention,the Remote mode is available only when indicated for the specific control loop.

The control loops provide "bumpless" transfer between Manual and Local Auto modes, such that when a control loop changes modes, the algorithm or the output is set so that there is not a step change in the output value. In general, this means that while in Manual mode, the PID algorithm setpoint is set to equal the process variable value. When in either Local or Remote Auto mode, the Manual output value tracks the PID algorithm output value. Notably, some control loops have automatic mode selection during the startup sequence, as indicated below.

Figure 9A:
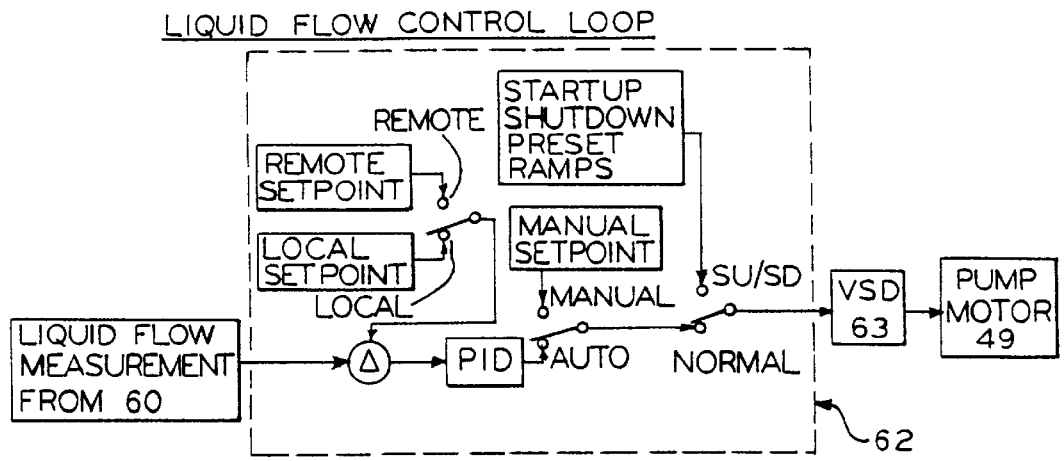
FIG. 9A is a schematic representation of the Liquid Flow Control Loop of the controller of an embodiment of the present invention.

The Liquid Flow Control Loop of FIG. 9A controls the liquid flow through the apparatus by monitoring the liquid flow rate via flowmeter 60 near the pump discharge and delivering as its output a signal to pump (VSD) controller 63. This loop receives a remote setpoint from an analog input set by an external control system.

Figure 9B:
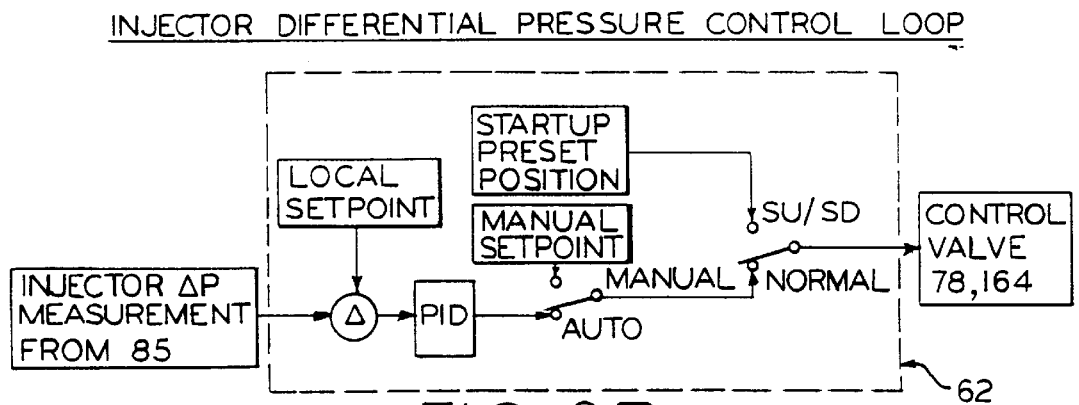
FIG. 9B is a schematic representation of the Injector Differential Pressure Control Loop of the controller of an embodiment of the present invention.

The Injector Differential Pressure Control Loop of FIG. 9B controls the pressure drop across injector 74, 74' by monitoring the signal generated by transmitter 85 and delivering as its output a signal to injector bypass control valve 78, 164. This control loop has no remote mode.

Figure 9C:
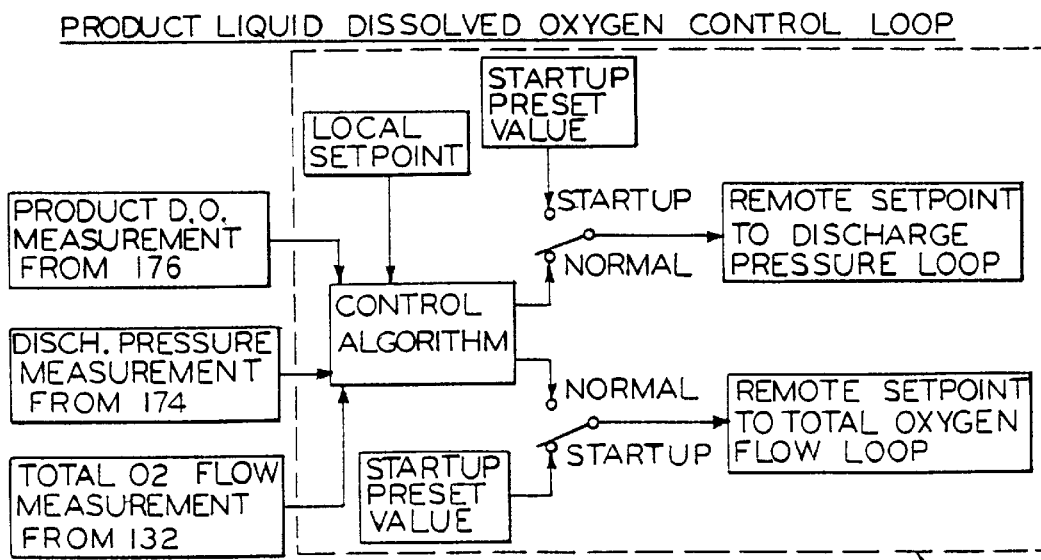
FIG. 9C is a schematic representation of the Product Liquid Dissolved Oxygen Control Loop of the controller of an embodiment of the present invention.

The Product Liquid Dissolved Oxygen Control Loop of FIG. 9C controls the level of dissolved oxygen in the product liquid by monitoring the signal from transmitter 179 corresponding to the dissolved oxygen level as sensed by sensor 176, the pressure of separator tank 114, 114' and/or the oxygen inlet flow measurement signal from mass flow meter 132, and delivering as its output the remote setpoint of the Oxygen Inlet Flow Control Loop (FIG. 9D) and/or the Discharge Pressure Control Loop (9E). The Product Liquid Dissolved Oxygen Control Loop employs a "Control Algorithm" which generates the output based on a comparison of the inputs it performs and through use of a PID algorithm.

Figure 9D:
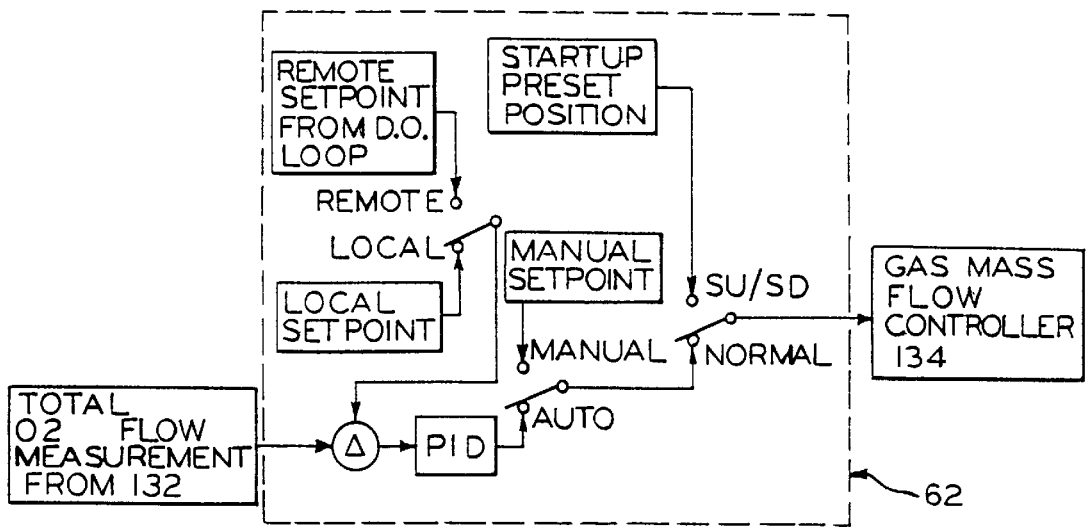
FIG. 9D is a schematic representation of the Total Oxygen Flow Control Loop of the controller of an embodiment of the present invention.

The Oxygen Inlet Flow Control Loop of FIG. 9D controls the oxygen flow rate to the apparatus by monitoring the signal from transmitter 132 corresponding to the oxygen mass flow of the combined source and recycled oxygen into the injector and delivering as its output a signal to valve 134. The remote setpoint is provided by the Product Liquid Dissolved Oxygen Control Loop (FIG. 9C) as discussed above or, alternatively, from an analog input set by an external control system.

Figure 9E:
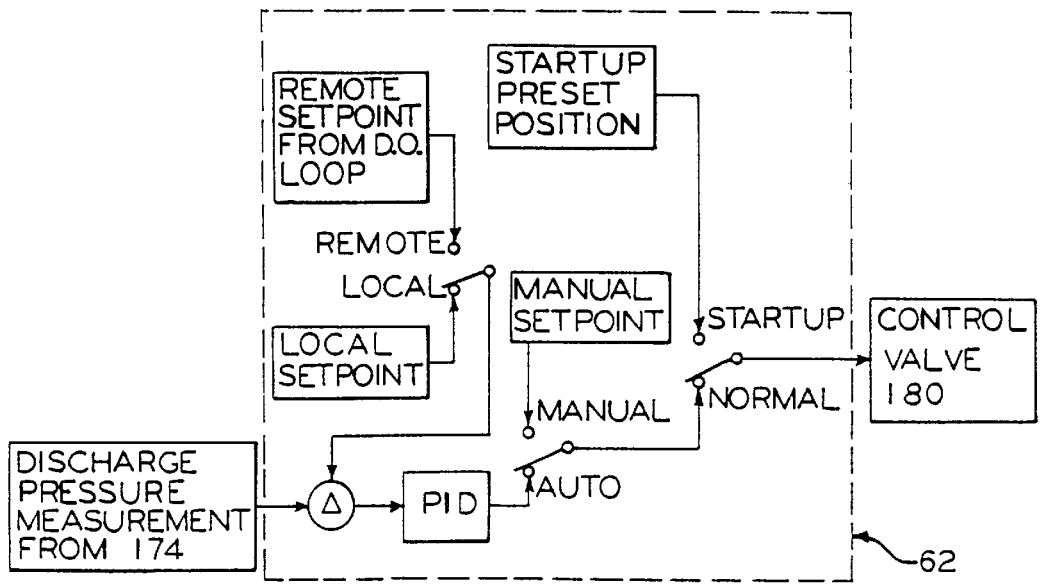
FIG. 9E is a schematic representation of the Discharge Pressure Control Loop of the controller of an embodiment of the present invention.

The Discharge Pressure Control Loop of FIG. 9E controls the pressure of the oxygenated product liquid by monitoring the pressure at gas separator tank 111, 114' via transducer 174 and delivering as its output as signal to valve 180 for controlling the discharge from the apparatus. The remote setpoint is provided by the Product Liquid Dissolved Oxygen Control Loop (FIG. 9C) as discussed above or, alternatively, from an analog input set by an external control system.

In addition to the above-mentioned analog measurements used for control, there are several process variables which may also be monitored to provide a better understanding of how the system is operating. These variables can be used, for example, to establish long range effects on the process or to indicate the need for maintenance. In general, monitoring loops may be provided which take a process measurement and convert it to an electrical signal that is connected to an analog input point in PLC 62, the PLC can then use the value for additional processing such as alarms and/or provide the value to the MMI for display and trend recording. The following process variables may be inputs to the monitoring loops: injector 74, 74' inlet liquid temperature, separator tank 114, 114' output temperature and outlet pressure from, e.g., pressure transducer 174; oxygen source flow rate from, e.g., oxygen flow meter 130; oxygen source flow pressure in line 124 upstream of valve 131; and total (source plus recycled) oxygen flow pressure and temperature in line 124 downstream of valve 131.

All of the analog inputs, including those used for control or as remote setpoints, may be provided with four alarm setting denoted as Low-Low, Low, High, and High-High. These settings may be adjusted by the operator using a screen of the MMI which limits the setting so that the Low-Low setting is between a minimum value and the Low setting, the Low setting is between the Low-Low setting and the High setting, the High setting is between the Low setting and the High-High setting, and the High-High setting is between the High setting and a maximum value. These alarms may be controlled by the MMI without reliance on the PLC. The Low-Low and High-High alarms should be latched so that if they are used for shutdown conditions, the condition that caused the shutdown can be determined. The Low and High alarms should not be of the latching type.

The discrete control logic for the present invention provides startup and shutdown sequencing and monitoring for equipment protection and is performed in PLC 62. Most of the input signals for this logic come from process or operator switches that provide a discrete, on/off input. Some of the signals for these operations are derived from the analog monitoring and control loops using adjustable setpoints compared against the analog measurements to generate a discrete value. These comparisons are performed by PLC 62 using setpoints entered at the MMI. The startup sequence may also be affected through the use of configuration switches that are set by the operator at the MMI. The configuration switches indicate which of the three above disclosed embodiments are set up in the apparatus. For example, if apparatus 10 (FIG. 1) is set up according to the third configuration without an injector bypass, setting the configuration switch to "Configuration 3" the conditions associated with the injector differential pressure loop (FIG. 9B) are disregarded.

The major functions of the discrete logic control are startup and shutdown operation; pump protection; system protection; and emergency stops using pushbuttons. The objective of the startup sequence is to safely start the apparatus and bring it to the desired operating conditions with a minimum of operator intervention. The desired operating conditions can be set by the operator prior to starting the unit or, alternatively, can be the last settings prior to the previous shutdown. The definition of the desired operating conditions include the controller states for the control loops of FIGS. 9A–9E (i.e., Manual, Local Auto or Remote Auto), and the controller setpoints for Local Auto control or output values for Manual control. The objective of the shutdown sequence is to ensure that the apparatus is safely and expediently brought to a stopped condition. The condition causing the shutdown should be latched for alarm indication, and other potential shutdown conditions should then be "latched-out" so that they cannot provide a false indication of why a shutdown occurred.

The system can be started up or shut down either from the MMI or by using remote isolated contact inputs. For example, in order to start up, the controller may require that the following conditions be met: a source oxygen pressure transmitter (not shown) in fluid communication with oxygen supply tube 124 upstream of valve 131 indicates an oxygen source pressure of at least 30 psig (a Low-Low alarm value); a pump suction low pressure switch (not shown) in pipe portion 44 indicates that the pump inlet pressure is normal; a pump recycle high flow switch (not shown) in pipe portion 58 indicates that any pump bypass flow through valve 56 is below the switch's trip point; the emergency stop buttons (not shown) are not pushed; and that all abnormal shutdown conditions have been reset. If these conditions are all met and the apparatus is in its Local Auto mode and the "Start" button is pressed, the apparatus begins its startup sequence. If these conditions are all met and the unit is instead in its Remote Auto mode and a "Remote Start" discrete input is received by PLC 62 from a remote controlling device, the apparatus begins its startup sequence.

The startup sequence may comprise the following ten steps. The parameters (e.g., 50%, 100 SCFH, 1% per second) identified in this example sequence are configurable and will have hard-coded high and low limits to ensure the equipment does not operate outside of reasonable limits. The ten steps are: (1) The Discharge Pressure Control Loop (FIG. 9E) is bypassed and valve 180 is opened to 50%. (2) The Liquid Flow Control Loop (FIG. 9A) is bypassed and pump VSD controller 63 is commanded to 25% of maximum output to ensure a "soft start" of the system. (3) The Product Liquid Dissolved Oxygen Control Loop (FIG. 9C) is bypassed and its outputs are set to 100 SCFH. (4) Pump 48 is started. The "Unit Running" logical switch is turned on and the "Startup" logical switch is turned on. (5) Pump VSD controller 63 ramps up at a rate of 1% per second up to a limit of 90% of maximum output. (6) When the pressure drop across injector 74 reaches either 15 psig or the setpoint of the Injector Differential Pressure Control Loop (FIG. 9C), or the injector inlet pressure exceeds a predetermined low alarm setpoint, Liquid Flow Control Loop (FIG. 9A) is entered in its previous control state (Manual, Local Auto or Remote Auto), and Discharge Pressure Control Loop (FIG. 9E) is entered in its previous control state (Manual, Local Auto or Remote Auto). (7) Automatic shutoff valve 126 is opened and the pressure from the oxygen source must exceed a low alarm setting of 30 psig. (8) The Oxygen Inlet Flow Control Loop (FIG. 9D) is bypassed and the output to valve 134 is commanded to 100%. Oxygen vent valve 122 is opened and oxygen is admitted into the system for 20 seconds. Valve 122 is then closed, and the Oxygen Inlet Flow Control Loop is entered in it previous control state (Manual, Local Auto or Remote Auto). (9) Thirty (30) seconds after the Oxygen Inlet Flow Control Loop is entered, the Product Liquid Dissolved Oxygen Control Loop (FIG. 9C) is put in its desired or previous state (Manual or Local Auto). (10) The "Startup" logical switch is turned off and the "Unit Running" switch remains on.

The discrete logic control may allow the shutdown sequence to be initiated by any of the following activities or process events: the injector inlet pressure, as sensed by an injector inlet pressure transmitter (not shown) fluidly connected to pipe portion 64, falls below a "Low-Low" or rises above a "High-High" alarm value after normal operating conditions have been attained; the total oxygen flow, as sensed by oxygen mass flow meter 132, falls below a "Low-Low" or rises above a "High-High" alarm value after normal operating conditions have been attained; the source oxygen pressure, as sensed by an oxygen pressure transmitter (not shown) fluidly connected to oxygen supply tube 124 upstream of valve 131, falls below a "Low-Low" or rises above a "High-High" alarm value after normal operating conditions have been attained; a pump suction low pressure switch (not shown) fluidly connected to pipe portion 44 senses that pump suction pressure is too low (below the switch's trip point); a pump recycle high flow switch (not shown) fluidly connected to pipe portion 58 senses that pump recirculation flow is too high (above the switch's trip point) the system is in Local Auto mode and the "Stop" button on the MMI is pressed; or the system is in Remote Auto mode and a "Remote Stop" input is received by PLC 62. If any of these conditions are met the normal shutdown sequence would begin.

The normal shutdown sequence may comprise the following steps: (1) The "Startup/Shutdown" logical switch is turned on and the "Unit Running" logical switch is turned off. Valve 126 is closed, pump 48 is ramped down at a configurable rate of 10% per second and, at the same time, dissolved oxygen analyzer 179 is shut off. (2) When the liquid flow rate, as sensed by flowmeter 60, is less than 10 gpm pump 48 is shut off and valve 180 is closed. (3) All PID loops stop processing so that they do not try to control a process which is not running. (4) The "Startup/Shutdown" logical switch is turned off.

The discrete logic control also provides pump protection. Pump 48 is protected from operating outside its range by three devices: valve 56, which controls the discharge pressure and limits it to a maximum of about 150 psig; a pump recycle high flow switch (not shown) in fluid communication with pipe portion 58 which detects excessively high (above the switch's trip point) liquid flow therethrough and shuts down the system; and a pump suction low pressure switch (not shown) in fluid communication with pipe portion 44 which detects that there is insufficient (below the switch's trip point) suction pressure for pump 48 and shuts down the system. The two switches are monitored by PLC 62 and used to determine when to shut down the system using the normal shutdown sequence described above. If a shutdown occurs based on either of these two switches being tripped, the condition is latched so that it can be displayed as an alarm on the MMI.

The discrete logic control also provides system protection and may initiate the shutdown sequence if any of the following conditions occur. Prior to shutdown, an "early warning" alarm may be issued to indicate that a shutdown may be imminent, with the condition causing the potential shutdown latched for alarm indication. These conditions, for example, may initiate the shutdown sequence: (1) An injector liquid inlet pressure transmitter (not shows) senses the pressure there is less than 40 psig or less than 5 psig more than the injector differential pressure sensed by transmitter 85 after startup of the apparatus is completed. This condition may be indicative of a pipe rupture upstream of the injector. (2) Oxygen flow meter 130 indicates higher than 200 SCFH or less than 20 SCFH after startup is completed. This condition may be indicative of an oxygen line break or oxygen flow controller failure. (3) A source oxygen pressure transmitter (not shown) in fluid communication with oxygen supply tube 124 reads less than 25 psig. This condition may be indicative of an insufficient source of oxygen, reducing or eliminating the efficacy of the apparatus. (4) The above oxygen pressure transmitter reads greater than 100 psig. This condition may be indicative of a source oxygen regulation problem that could be hazardous to the system as a whole due to overpressurization of the process. Additionally, the discrete logic control may also control the operation of oxygen vent valve 122, which may be opened for a period of, for example, 0.25 seconds every minute. Further, a button on the MMI may be provided to open valve 122 in response to its being pushed.

The apparatus may also be provided with at least one and preferably two emergency stop buttons hardwired into the electrical controls for immediately removing power from the active devices of the apparatus. Pressing an emergency stop button causes an immediate "uncontrolled" shutdown of the apparatus uncontrolled by PLC 62 by automatically disconnecting power from the pump and the process control devices.

In operation, the oxygenation process which takes place in apparatus 10, 10' is described herein above as comprising the formation of a shockwave for mixing the liquid and oxygen. In the operation of an apparatus 10 embodiment comprising either the first or second injector/diffuser/absorber configurations, shockwave 196 is formed in first diffuser portion 100 which aids in intermixing the oxygen and liquid by providing a large boundary surface area between the liquid and the oxygen bubbles (Fig,. 4). Similarly, in the operation of apparatus 10 or 10' comprising the third injector/diffuser/absorber configuration, shockwave 196 is formed in first diffuser portion 100' (FIG. 7). It has been found that in order for the shockwave to occur in first diffuser portion 100, 100' the liquid flow velocity through throat 94, 94' must exceed approximately 30 meters per second. Shockwave 196 is produced as the 80 to 90 psig liquid upstream of injector throat 94, 94' is flowed therethrough and converted to a 40 to 50 psig liquid downstream of the throat. The energy lost in the pressure reduction from about 90 psig to about 50 psig is, in part, transformed into the energy which creates shockwave 196, creates bubble surface area and compresses the oxygen entering at the throat.

Oxygen is provided to throat 94, 94' of injector 74, 74' in the manner described above. The flow rate of oxygen to the throat may be varied to achieve different concentration levels of dissolved oxygen. Notably, if no oxygen is provided, cavitation may occur within injector 74, 74', which, over time, may be detrimental to its performance. To achieve maximum dissolved oxygen levels, the quantity of oxygen supplied to the injector should be at least the amount necessary to saturate the liquid flowing therethrough. For example, in order to saturate water at 50 psig and 70° F. (to a maximum concentration of 193 mg/l) flowing through apparatus 10 at a flow rate of 135 gpm, an oxygen flow rate of at least 158 standard cubic feet per hour (SCFH) must be provided to the injector throat. Any excess oxygen introduced into the injector can be recycled through tube 118 from gas separator tank 114 back into injector 74 as described above.

The shockwave breaks the admixture of liquid and a plurality of large oxygen bubbles into an admixture of liquid and greater plurality of smaller bubbles in first diffuser portion 100, 100'. There is pressure recovery downstream of the shockwave. The plurality of smaller bubbles proceeds downward with the flowing liquid into second diffuser/absorber portion 102, 102', in which the pressure of the admixed liquid and oxygen phases is increased again. In the first and second diffuser/absorber portions, the linear pressure gradient normally associated with increasing liquid depth in a static fluid is augmented, providing increases in the pressure of and pressure gradient in the liquid and gas phases higher than would otherwise be experienced. The augmented pressure increase occurring in the first and second diffuser/absorber portions increases the driving force between the gas and liquid phases, increases the concentration of oxygen molecules at the liquid-gas interface and increases the buoyancy of the bubbles in the liquid, causing some of them to float upwards against the downward liquid flow. The oppositely directed flow of oxygen bubbles and liquid promotes their intermixing. Further, the high relative velocity between the oxygen bubbles and the liquid, and the turbulent mixing thereof, keeps the liquid molecule concentration gradient at the liquid-gas interface high. The oxygen molecule concentration of a bubble, however, is fixed by the pressure acting thereon. The differences in concentrations between the gas and the liquid at their interface promotes the absorption of the oxygen into the liquid, allowing the gas to penetrate the boundary surface between the two phases.

The upwardly floating small bubbles in first diffuser portion 100, 100' and second diffuser portion 102, 102' are broken up into a greater plurality of even smaller bubbles, further increasing the surface area of the liquid-oxygen interface and mixing the liquid and oxygen. Without wishing to limit the scope of the present invention, it is surmised that at least some of the upwardly floating bubbles are broken up into smaller bubbles by means of their contacting shockwave 196. The residence time of oxygen bubbles in the liquid is also increased by their countercurrent flow in the liquid in the diffuser/absorber, thus allowing greater residence time for the gas to be absorbed into the liquid.

The cycle of oxygen bubbles being broken up into a greater plurality of smaller bubbles in first diffuser portion 100, 100' and second diffuser portion 102, 102', the bubbles flowing with the downflowing liquid into second diffuser/absorber portion 102, 102', the bubbles' pressure and buoyancy increasing in the first and second diffuser portions, the bubbles floating upwards against the downward liquid flow, and the bubbles being broken up into a greater plurality of even smaller bubbles continues until the oxygen bubbles are small enough to flow cocurrently with the liquid phase from second diffuser/absorber portion 102, 102' to pipe absorber 104, 142. The expected bubble size in solution is 25 to 60 μm.

The oxygen enriched liquid slowly flows through large diameter pipe absorber 104, 142 under an approximately constant pressure equivalent to that at the outlet of second diffuser/absorber portion 102, 102'. In the pipe absorber, further residence time is provided for the oxygen to even more fully enter solution, the driving force provided almost entirely by the pressure acting on the admixture and the difference between the actual and potential (saturation) oxygen concentrations. Because of the smaller relative velocity between the gas and liquid, mixing occurs to a lesser degree in the pipe absorber. Rather, mass transfer is accomplished therein by adsorption under pressure and mixing of the liquid phase. As described above, oxygen enriched liquid discharge from the pipe absorber flows into tank 114, 114', through valves 180, 184, 186, after which it is recovered from the apparatus and, for example, bottled using well known techniques.

It can be understood from the above description that the inventive process is, basically, a two step process: The first step is the creation of small oxygen bubbles into the supply liquid with the aid of a shockwave in the first diffuser portion and, in some embodiments, turbulent mixers provided in the pipe absorber. The second step is the absorption of small gas bubbles in solution with the liquid, accomplished in the first and second diffuser portions and the pipe absorber.

While this invention is disclosed as having particular dimensions and flow rate capacities, it is expected that the above described embodiments may be appropriately scaled up or down to provide larger or smaller sized embodiments of the present invention having higher or lower flow rates, but which produce oxygenated liquids having oxygen concentrations equivalent to liquids prepared by above described apparatus 10, 10'.

Further, while this invention has been described as having a preferred design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An apparatus for oxygenating a liquid, comprising:
    a liquid pump;
    supply piping having an inlet connected to said pump and an outlet;
    an injector having a liquid inlet forming a nozzle, a liquid outlet and an oxygen inlet, said oxygen inlet intermediate said liquid inlet and said liquid outlet, said outlet of said supply piping connected to said liquid inlet of said injector, said injector arranged such that said injector liquid inlet is above said injector liquid outlet;
    a first diffuser having an inlet, an outlet and a diverging inside surface, said injector liquid outlet connected to said first diffuser inlet, said first diffuser inlet above said first diffuser outlet;
    a second diffuser having an inlet, an outlet and a diverging inside surface, said second diffuser outlet larger than said first diffuser outlet, said second diffuser inlet above said second diffuser outlet, said second diffuser inlet in fluid communication with said first diffuser outlet, whereby a liquid is conducted from said pump through said supply piping and downward through said injector and said first diffuser to said second diffuser; and
    a variable liquid pressure regulating device located downstream of said second diffuser outlet, oxygenated liquid being conducted through said liquid pressure regulating device, the flow of liquid flowing through said apparatus being variably restricted by said liquid pressure regulating device, whereby the pressure of the liquid in said apparatus is regulated.

2. The apparatus of claim 1, wherein said injector liquid inlet is vertically above said injector liquid outlet.

3. The apparatus of claim 1, wherein said first diffuser inlet is vertically above said first diffuser outlet.

4. The apparatus of claim 1, further comprising an absorber having an inlet and an outlet, said absorber inlet in fluid communication with said second diffuser outlet.

5. The apparatus of claim 4, wherein said absorber comprises an elongate portion, said absorber outlet located below said absorber inlet.

6. The apparatus of claim 4, wherein the configuration of said absorber is serpentine.

7. The apparatus of claim 4, further comprising at least one mixer disposed in said absorber.

8. The apparatus of claim 1, wherein one of said inside surfaces of said first and said second diffusers is frustoconical.

9. The apparatus of claim 1, wherein said first diffuser outlet is adjacent said second diffuser inlet, said first diffuser outlet equivalent in size and shape to said second diffuser inlet.

10. The apparatus of claim 1, wherein said first and said second diffusers comprise a single diffuser having an inlet in fluid communication with said injector liquid outlet, an outlet and a diverging inside surface, said single diffuser outlet larger than said single diffuser inlet, said single diffuser outlet located below said single diffuser inlet.

11. The apparatus of claim 1, wherein said injector comprises a venturi having a throat, said gas inlet communicating with the throat of said venturi.

12. The apparatus of claim 11, wherein said venturi comprises said first diffuser, said first diffuser inlet adjacent said venturi throat.

13. The apparatus of claim 1, further comprising a gas separator in fluid communication with said second diffuser outlet, said gas separator having means for recovering oxygen and directing the recovered oxygen to said injector gas inlet.

14. An apparatus for oxygenating a liquid, comprising:
    a liquid pump;
    supply piping having an inlet connected to said pump and an outlet;

an injector having a liquid inlet forming a nozzle, a liquid outlet and an oxygen inlet, said oxygen inlet intermediate said liquid inlet and said liquid outlet, said outlet of said supply piping connected to said liquid inlet of said injector;

a first diffuser having an inlet, an outlet and a generally diverging inside surface, said injector liquid outlet connected to said first diffuser inlet;

an absorber having an inlet and an outlet, said absorber inlet in fluid communication with said first diffuser outlet; and an injector bypass adapted to conduct a portion of the liquid conveyed through said supply piping around said injector, said bypassed liquid portion mixed with oxygenated liquid from said injector at a point downstream of said injector;

whereby the throughput flow capacity of said apparatus may be increased by diverting said portion of the liquid flow from passage through said injector, said portion conducted through said injector bypass.

15. The apparatus of claim 14, wherein said first diffuser inside surface is frustoconical.

16. The apparatus of claim 14, further comprising a second diffuser intermediate said first diffuser and said absorber, said second diffuser having an inlet, an outlet and a generally diverging inside surface.

17. The apparatus of claim 16, wherein said injector bypass comprises a conduit fluidly connecting said supply piping, at a location intermediate said pump and said injector liquid inlet, and an element intermediate said first and said second diffusers.

18. The apparatus of claim 17, wherein said element is generally cylindrical, and said injector bypass conduit has an outlet centrally disposed within said element.

19. The apparatus of claim 18, wherein said injector bypass conduit outlet comprises a nozzle.

20. The apparatus of claim 14, wherein said injector bypass further comprises a valve located on said injector bypass conduit, said valve adapted to regulate the flow of liquid through said injector bypass conduit.

21. The apparatus of claim 14, wherein said injector bypass comprises a conduit fluidly connecting said supply piping, at a location intermediate said pump and said injector liquid inlet, and an element intermediate said absorber and an outlet from said apparatus.

22. The apparatus of claim 14, wherein the configuration of said absorber is serpentine.

23. The apparatus of claim 14, further comprising at least one mixer disposed in said absorber.

24. The apparatus of claim 14, further comprising a gas separator in fluid communication with said absorber outlet, said gas separator having means for recovering oxygen and directing the recovered oxygen to said injector gas inlet.

\* \* \* \* \*